United States Patent [19]

Pirotte et al.

[11] Patent Number: 5,459,138
[45] Date of Patent: Oct. 17, 1995

[54] PYRIDOTHIADIAZINES

[75] Inventors: Bernard Pirotte, Oupeye; Pascal de Tullio, Jupille; Bernard Masereel, Libin; Jacques Delarge, Dolembreux, all of Belgium; Jean Lepagnol, Chaudon; Pierre Renard, Versailles, both of France

[73] Assignee: Adir Et Compagnie, Courbevoie, France

[21] Appl. No.: 217,192

[22] Filed: Mar. 24, 1994

[30] Foreign Application Priority Data

Mar. 26, 1993 [FR] France .................. 93 03458

[51] Int. Cl.$^6$ .................. C07D 513/04; A61K 31/54
[52] U.S. Cl. .................. 514/222.8; 544/10
[58] Field of Search .................. 544/10; 514/222.8

[56] References Cited

U.S. PATENT DOCUMENTS 3,157,647  11/1964  Sheehan .................. 260/243
3,288,678  11/1966  deStevens .................. 544/11

FOREIGN PATENT DOCUMENTS 1368948  11/1991  United Kingdom.

OTHER PUBLICATIONS

*Physicians' Desk Reference*, pp. 1826–1830 (1995).
Copani, *Nootropic Drugs Positively Modulate α–Amino–3–Hydroxy–5–Methyl–4–Isoxazolepropionic Acid–Sensitive Glutamate Receptors in Neuronal Cultures*, Journal of Neurochemistry vol. 58, No. 4, 1199–1204 (1992).
*Index Nominum, International Drug Directory 1992/1993*, edited by the Swiss Pharmaceutical Society, listing for Piracetam (1992).
Goodman and Gilman, *The Pharmacological Basis of Therapeutics*, eighth edition, pp. 718–721 (1990).
Kotovskaya et al., Khim.–Farm. 2h. (1979), vol. 13, No. 4, pp. 54–57, and English Abstract.
S. K. Kotovskaya, et al., Chemical Abstracts 91, No. 5, 91:39441y: Synthesis and properties of pyrido[2,3–3]–1,2, 3–thiadiazine 1,1–dioxides, p. 631 (1979).
Kanji Noda, et al., Chemical Abstracts 87, No. 9, 87:68437z: Pyridothiadiaxines, p. 56 (1977).
J. Delarge, et al., Chemical Abstracts 83, No. 7, 58608j: Synthesis and pharmacological properties of some N–acylsulfonamides, p. 483 (1975).

*Primary Examiner*—John M. Ford
*Attorney, Agent, or Firm*—The Firm of Gordon W. Hueschen

[57] ABSTRACT

The invention relates to a compound selected from those of formula (I):

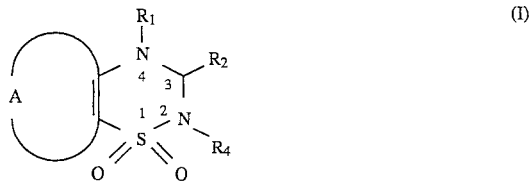

in which A, $R_1$, $R_2$ and $R_4$ are as defined in the description, and medicinal products containing the same which is useful for treating a pathology related to dysfunctioning of glutamatergic neurotransmission.

14 Claims, No Drawings

PYRIDOTHIADIAZINES

The present invention relates to new pyridothiadiazines, to processes for their preparation and to the pharmaceutical compositions which contain them.

It is now recognized that excitatory amino acids, and very particularly glutamate, play a crucial role in physiological neuronal plasticity processes and in the mechanisms which underlie learning and memory. Recently, pathophysiological studies have clearly shown that a deficiency in glutamatergic neurotransmission is closely associated with the development of Alzheimer's disease (Neuroscience and Biobehavioral Reviews, 1992, 16, 13–24; Progress in Neurobiology, 1992, 39, 517–545) or at the time of cerebral aging (Brain Research, 1992, 589, 320–326).

Moreover, much work during recent years has shown the existence of receptor subtypes for excitatory amino acids and of their functional interactions (Molecular Neuropharmacology, 1992, 2, 15–31).

The AMPA ("α-amino-3-hydroxy-5-methyl-4-isoxazolepropionic acid") receptor appears, among these receptors, to be the most involved in physiological neuronal excitability phenomena and especially in those involved in memorization processes. For example, learning has been shown as being associated with the increase in the binding of AMPA to its receptor in the hippocampus, one of the cerebral regions essential to memory-cognitive processes (Brain Research, 1992, 573, 228–234, Behavioral and Neural Biology, 1992, 58, 222–231). Nootropic agents such as aniracetam have likewise very recently been described as positively modulating AMPA receptors of neuronal cells (Journal of Neurochemistry, 1992, 58, 1199–1204).

The Applicant has now discovered new pyridothiadiazines which surprisingly have a powerful facilitating activity on the AMPA current, which therefore appear useful to the clinician in the treatment of pathologies involving the AMPA receptor. For example, it has been shown that the sensitivity of the AMPA receptor decreases at the time of cerebral aging (Hippocampus, 1992, 2, 457–468). Pyridothiadiazines, described in the publication Kotovskaya et al., Khim. - Farm. 2h. (1979), Vol. 13, No. 4, pp 54–57, are known from the prior art.

Other pyridothiadiazines are also described in Patent Application FR 2,267,775 as diuretics.

More particularly, the invention relates to the compounds of formula (I):

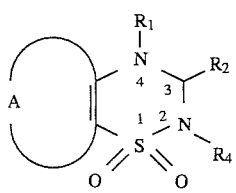

in which:

$R_1$ represents a group chosen from:

hydrogen, $R_3$, with $R_3$ representing a radical chosen from lower alkyl, lower alkenyl and lower alkynyl, $R_3$ being unsubstituted or substituted, cycloalkyl, substituted cycloalkyl, lower cycloalkylalkyl, substituted lower cycloalkylalkyl, lower acyl, lower alkoxycarbonyl, arylcarbonyl which is unsubstituted or substituted on the aryl ring, aryloxycarbonyl which is unsubstituted or substituted on the aryl ring, or $R_1$ forms, between the 3 or 4 atoms of the thiadiazine ring present in the formula (I), a double bond;

$R_2$ represents a group chosen from:

hydrogen, $R_{10}$, with $R_{10}$ having the same definition as $R_3$ above, $R_{10}$ being unsubstituted or substituted, $R_{11}$, with $R_{11}$ representing a group chosen from cycloalkyl, lower cycloalkylalkyl, bicycloalkyl and lower bicycloalkylalkyl, $R_{11}$ being unsubstituted or substituted, —O—$R_{10}$, with $R_{10}$ as defined above, thioxo, —S—$R_{12}$, in which $R_{12}$ represents a lower alkyl, $R_{12}$ being unsubstituted or substituted, aryl, substituted aryl,

in which $R_8$ and $R_9$ represent, independently of one another, a radical chosen from:

hydrogen, lower alkyl, cycloalkyl, lower cycloalkylalkyl, a heterocycle $R_{13}$ chosen from pyrrolidine, piperidine, piperazine, morpholine and thiomorpholine;

or form, together with the nitrogen atom which carries them, a heterocycle $R_{13}$ as defined above, $R_4$ represents a group chosen from:

hydrogen, $R_{14}$, $R_{14}$ having the same definition as $R_3$ above, $R_{14}$ being unsubstituted or substituted, cycloalkyl, aryl, substituted aryl, lower acyl, lower alkoxycarbonyl, arylcarbonyl, unsubstituted or substituted on the aryl ring, aryloxycarbonyl, unsubstituted or substituted on the aryl ring, or $R_4$ forms, between the 2 and 3 atoms of the thiadiazine ring present in the formula (I), a double bond;

A forms, with the two carbon atoms which carry it, a pyridine ring chosen from the $A_1$, $A_2$, $A_3$ and $A_4$ groups:

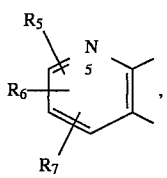

(A₁)

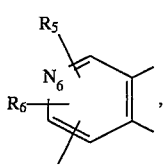

(A₂)

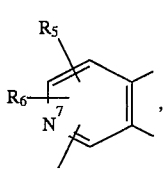

(A₃)

and

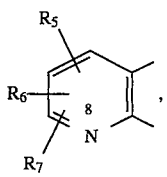

(A₄)

in which $R_5$, $R_6$ and $R_7$ represent, independently of one another, a radical chosen from: hydrogen, halogen, lower alkyl, hydroxyl, mercapto, lower alkoxy, lower alkylthio, trifluoromethyl, carboxyl, lower acyl, aryl, lower arylalkyl, amino, lower alkylamino and lower dialkylamino, it being understood that, when A represents an unsubstituted group of formula $A_1$, $R_2$ represents a hydrogen atom, an amino radical or a methyl radical, and $R_5$, $R_6$ and $R_7$ simultaneously represent hydrogen atoms, then $R_1$ cannot be a hydrogen atom or a methyl radical, it being understood that, except when otherwise specified, "lower alkyl", "lower alkoxy", "lower acyl" and "lower alkylthio" mean linear or branched groups containing 1 to 6 carbon atoms, "lower alkenyl" means a linear or branched group containing 2 to 6 carbon atoms comprising from 1 to 2 double bonds;

"lower alkynyl" means a linear or branched group containing 2 to 6 carbon atoms comprising from 1 to 2 triple bonds, "cycloalkyl" means a cyclic group containing 3 to 8 carbon atoms, "bicycloalkyl" means a bicyclic group containing 6 to 12 carbon atoms, "aryl" means phenyl or naphthyl, "substituted", in association with the $R_3$, $R_{10}$ and $R_{14}$ groups, means that these groups thus described are substituted by one or a number of radicals chosen from halogen, hydroxyl and lower alkoxy, "substituted", in association with the "cycloalkyl", "cycloalkylalkyl" and $R_{11}$ groups, means that this group thus described is substituted by one or a number of radicals chosen from hydroxyl, lower alkyl and lower alkoxy or is substituted by an oxo group, "substituted", in association with the aryl group, means that this group thus described is substituted by one or a number of radicals chosen from halogen, hydroxyl, lower alkyl, lower alkoxy and trifluoromethyl, to their optical isomers, and to their addition salts with a pharmaceutically acceptable acid or base.

Mention may be made, among pharmaceutically acceptable acids which can be used to form an addition salt with the compounds of the invention, as examples and in a non-limiting way, of hydrochloric, sulfuric, phosphoric, tartaric, malic, maleic, fumaric, oxalic, methanesulfonic, ethanesulfonic, camphoric and citric acids.

Mention may be made, among pharmaceutically acceptable bases which can be used to salify the compounds used according to the invention, as examples and in a non-limiting way, of sodium hydroxide, potassium hydroxide, triethylamine, diethylamine, ethanolamine, arginine, lysine and diethanolamine.

One aspect of the invention constitutes the process for the preparation of the compounds of formula (I), wherein a compound of formula (II):

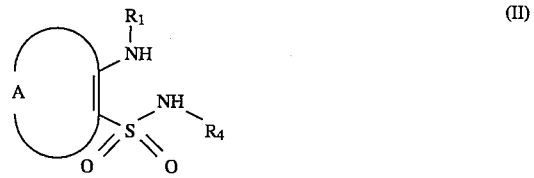

(II)

in which $R_1$, $R_4$ and A are as defined in the formula (I), is reacted a) either with a compound of formula (III)

(III)

in which $R_a$ represents a $R_{10}$, $R_{11}$, aryl or substituted aryl group, as defined in the formula (I), or, while hot, with a compound of formula (IV):

(IV)

to obtain the compounds of formula (I/a):

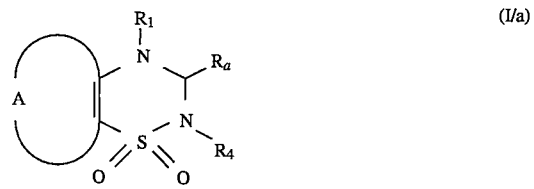

(I/a)

in which $R_1$, $R_4$, $R_a$ and A are as defined above, a specific case of the compounds of formula (I) in which $R_2$ represents a $R_a$ group, or with paraformaldehyde, ethyl orthoformate or a formic acid/acetic acid mixed anhydride, to obtain the compounds of formula (I/b):

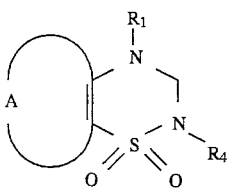
(I/b)

in which $R_1$, $R_4$ and A are as defined above, a specific case of the compounds of formula (I) in which $R_2$ represents a hydrogen atom,
or else,
 b) with urea to lead to the compounds of formula (V):

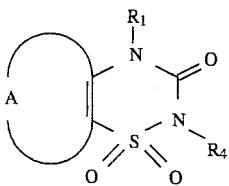
(V)

in which $R_1$, $R_4$ and A are as described above, which are then:
* salified and then reacted with a compound of formula (VI):

$R_{10}$—Hal (VI)

in which $R_{10}$ is as defined in the formula (I) and Hal represents a halogen atom,
to obtain a compound of formula (I/c):

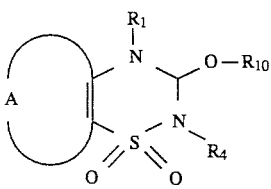
(I/c)

in which $R_1$, $R_4$, $R_{10}$ and A are as defined above, a specific case of the compounds of formula (I) in which $R_2$ represents a —O—$R_{10}$ group,
* or else subjected to a thiation agent to obtain the compound of formula (I/d):

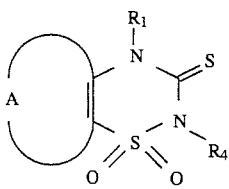
(I/d)

in which $R_1$, $R_4$ and A are as defined above, a specific case of the compounds of formula (I) in which $R_2$ represents a thioxo group,
which compound of formula (I/d) is reacted with a compound of formula (VI):

Hal'—$R_{12}$ (VI)

in which $R_{12}$ is as defined in the formula (I) and Hal' represents a halogen atom,
to obtain the compound of formula (I/e):

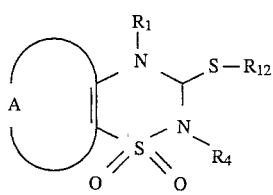
(I/e)

in which $R_1$, $R_4$, $R_{12}$ and A are as defined above, a specific case of the compounds of formula (I) in which $R_2$ represents an alkylthio group, which compounds of formula (I/e) can then be subjected to an amine of formula (VII):

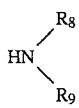
(VII)

in which $R_8$ and $R_9$ are as defined in the formula (I), to obtain the compounds of formula (I/f):

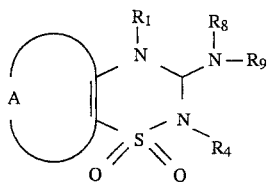
(I/f)

in which $R_1$, $R_4$, $R_8$, $R_9$ and A are as defined above, a specific case of the compounds of formula (I) in which $R_2$ represents a —$NR_8R_9$ group,
the compounds of formula (I/a) to (I/f) forming the combined compounds of formula (I),
it being understood that the compounds of formula (I/a), (I/b), (I/c), (I/e) and (I/f) can be, if appropriate, selectively reduced in order to obtain the corresponding compounds of formula (I) where the bond between the 2 and 3 atoms, or between the 3 and 4 atoms, of the thiadiazine ring is saturated,
it being possible for the compounds of formula (I) to be:
 purified according to one or a number of purification methods chosen from crystallization, chromatography on a silica column, extraction, filtration and passing through charcoal or resin,
 separated, in the pure form or in the mixed form, into their possible optical isomers,
 and salified with a pharmaceutically acceptable acid or base.

The invention also comprises the process for obtaining the compounds of formula (I/a):

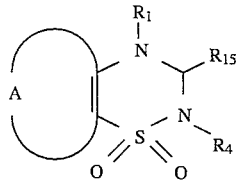
(I/a)

in which $R_1$, $R_4$ and A are as defined in the formula (I) and $R_{15}$ represents a $R_{10}$ or $R_{11}$ group as defined in the formula (I),
wherein:
a compound of formula (II/a):

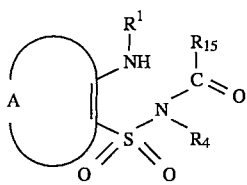

(II/a)

in which $R_1$, $R_4$, $R_{15}$ and A are as defined above,
is subjected to a cyclizing agent in order to obtain the corresponding compound of formula (I/a),
it being possible for the compounds of formula (I/a) thus obtained to be:

purified according to one or a number of purification methods chosen from crystallization, chromatography on a silica column, extraction, filtration and passing through charcoal or resin, separated, in the pure form or in the mixed form, into their possible optical isomers, and salified with a pharmaceutically acceptable acid or base.

Another aspect of the invention is also the process for the preparation of the compounds of formula (I/g):

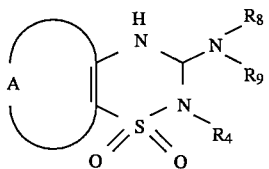

(I/g)

in which $R_4$, $R_8$, $R_9$ and A are as defined in the formula (I), a specific case of the compounds of formula (I) in which $R_2$ represents a —$NR_8R_9$ group and $R_1$ represents a hydrogen atom,
wherein:
either a compound of formula (II/b):

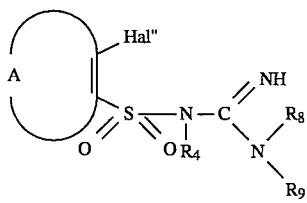

(II/b)

in which $R_4$, $R_8$, $R_9$ and A are as defined above and Hal" represents a halogen atom,
is reacted while hot in basic medium,
or a compound of formula (II):

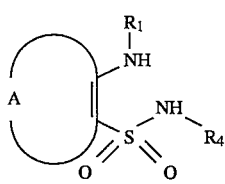

(II)

in which $R_1$, $R_4$ and A are as defined above, is reacted with a compound of formula (VIII):

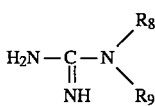

(VIII)

in which $R_8$ and $R_9$ are as defined above,
in order to obtain the corresponding compound of formula (I/g),
it being possible for the compounds of formula (I/g) to be:

purified according to one or a number of purification methods chosen from crystallization, chromatography on a silica column, extraction, filtration and passing through charcoal or resin, separated, in the pure form or in the mixed form, into their possible optical isomers, and salified with a pharmaceutically acceptable acid or base.

The invention also relates to the process for the preparation of the compounds of formula (I/h):

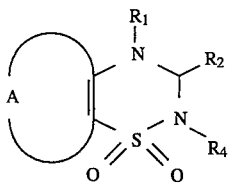

(I/h)

in which $R_1$, $R_4$ and A have the same meaning as in the formula (I), it being understood that at least one of the $R_1$ or $R_4$ substituents is other than a hydrogen atom,
wherein,
a compound of formula (I/i):

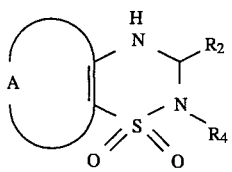

(I/i)

in which $R_2$, $R_4$ and A are as defined above, is reacted with a compound of formula (XI):

$R_1'$—X  (XI)

in which $R_1'$ has the same meaning as $R_1$ as defined in the formula (I) with the exception of hydrogen and X represents a leaving group, and/or, when $R_4$ represents a hydrogen atom, is reacted with a compound of formula (XII):

$R_4'$—X'  (XII)

in which $R_4'$ has the same meaning as $R_4$ as defined in the formula (I) with the exception of hydrogen and X' represents a leaving group,
it being possible for the compounds of formula (I/h) thus obtained to be:

purified according to one or a number of purification methods chosen from crystallization, chromatography on a silica column, extraction, filtration and passing through charcoal or resin, separated, in the pure form or in the mixed form, into their possible optical isomers, and salified with a pharmaceutically acceptable acid or base.

The starting materials used in the preceding processes are either commercially available or easily accessible to those skilled in the art according to processes known in the literature or proposed during the preparation examples described below.

The compounds of formula (II) are, for example, easily accessible to those skilled in the art by reacting a compound of formula (IXa):

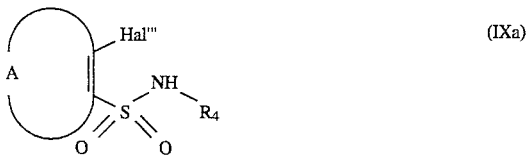

in which $R_4$ and A are as defined in the formula (I) and Hal''' represents a halogen atom, with an amine of formula (X):

in which $R_1$ is as defined in the formula (I).

The compounds of formula (II/a) are, for example, easily obtained by those skilled in the art by reacting a compound of formula (IXb):

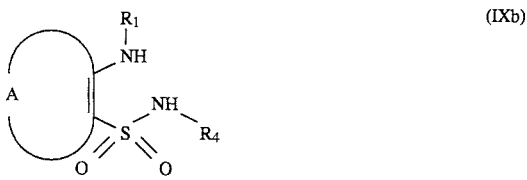

in which $R_1$ and A are as described in the formula (I), with a compound of formula (XI):

or of formula (XII):

in which $R_{15}$ represents a $R_{10}$ or $R_{11}$ group as defined in the formula (I), optionally followed by a controlled hydrolysis, when the product of the reaction has also been acylated on the nitrogen carrying the $R_1$ group.

The compounds of formula (II/b) are also, for example, easily accessible to those skilled in the art by reacting a compound of formula (IXc):

in which A is as defined above and Hal'' represents a halogen atom, with a compound of formula (XIV):

in which $R_4$, $R_8$ and $R_9$ are as defined in the formula (I).

Pyrido[3,2-e][1,2,4]thiadiazine 1,1-dioxides are also accessible from variously substituted 2-chloro-3-nitropyridines.

The introduction of a nitro group (into position 3, into position 5 or into positions 3 and 5) is generally carried out starting from a 2-aminopyridine. When position 5 is occupied, only the 3-nitro derivative is obtained. When position 5 is free, the mononitro compounds at 3 or 5 can obtained and separated, as well as the dinitro compound at 3 and 5.

When the 2-aminopyridine is not commercially available, a 2-hydroxypyridine can, in certain cases, be nitrated in an identical way. Moreover, 2-chloropyridines optionally give access to 2-aminopyridines.

Easily accessible substituents of the pyrido ring are alkyl, in particular methyl, radicals, amino, alkylamino and dialkylamino radicals, by reduction of a nitro functional group, trifluoromethyl radicals, halo, in particular chlorine and bromine, radicals, alkoxy, in particular methoxy, radicals and carboxyl and acyl radicals.

The compounds of the present invention have advantageous pharmacological properties since they can selectively potentiate excitatory electrophysiological phenomena induced by AMPA, either in Xenopus ovocytes expressing glutamate receptors by injection of rat cortex mRNA, or in the hippocampus during electrical stimulation of glutamatergic neurotransmission routes.

Electrophysiological studies carried out with respect to the excitability induced by AMPA expressed in Xenopus ovocytes or present naturally in the hippocampus have shown that these effects are always greater than those of the reference compounds and confer on the compounds of the invention pharmacological and therapeutic potentialities with respect to disorders induced by dysfunctioning of glutamatergic neurotransmission and especially related to the AMPA receptor.

Glutamatergic neurotransmission is now widely demonstrated as crucial for physiological processes of learning and memory, and more widely for processes controlling the faculties of attention, concentration and vigilance. More particularly, the receptor subtype known as AMPA seems to play a fundamental role in these processes. The compounds of the present invention have shown advantageous pharmacological effects since they can selectively facilitate the activation of this AMPA receptor. These effects are surprisingly much more intense than those of the reference compounds: diazoxide and aniracetam.

The compounds of the invention are therefore useful as agents which facilitate AMPA receptors and therefore constitute therapeutic agents for the treatment and prevention of pathologies related to dysfunctioning of glutamatergic neurotransmission such as:

memory-cognitive disorders associated with age and with anxiety or depressive syndromes, progressive neurodegenerative diseases such as, for example, Alzheimer's disease, Pick's atrophy, Huntington's chorea and schizophrenia, the aftereffects of acute neurodegenerative diseases such as, for example, ischemia and epilepsy.

The compounds have also proved to be advantageous in the treatment of diabetic-type pathologies, related to dysfunctioning of insulin secretion, which was recently described as regulated by AMPA receptors (British Journal of Pharmacology, 1992, 106, 354–359).

Another subject of the present invention is the pharmaceutical compositions containing a compound of general formula (I), or one of its salts with a pharmaceutically acceptable acid or base, in combination with one or a number of pharmaceutically acceptable excipients or vehicles.

Mention could be made, among pharmaceutical compositions according to the invention, as examples and in a non-limiting way, of those which are suitable for oral, rectal, nasal or parenteral administration and especially tablets, sugar-coated tablets, gelatin capsules, packets, chartulas, granules, pills, pellets, suppositories, creams, ointments, aerosols, capsules, dermal gels and injectable or drinkable solutions.

The dose varies from one individual to another, depending on the age, weight and sex of the patient, the administration route chosen and the nature and intensity of the ailment. The doses used range between 1 and 500 mg for one treatment, divisible into 1 to 3 doses per 24 h.

The following preparations are useful in the preparation of the compounds of the invention. They do not form part of the invention. Abbreviations used: M.p. (melting point), Yd. (Yield), eq. (equivalent).

PREPARATION 1:
3-AMINOPYRIDINE-2-SULFONAMIDE

The title compound is obtained according to the technique described in the literature [R. Lejeune et al., J. Pharm. Bel. (1984), Vol. 39, pp. 217–224].

PREPARATION 2:
4-AMINOPYRIDINE-3-SULFONAMIDE 15 g of 4-chloropyridine-3-sulfonamide are dissolved in 150 cm$^3$ of concentrated aqueous ammonia. The clear solution is saturated with a stream of gaseous ammonia for exactly half an hour before being introduced into a sealed tube. The tube is placed at 150° C. for 18 hours.

The reaction mixture is then cooled and concentrated on a rotary evaporator to a volume of 30 cm$^3$. The precipitate obtained is collected on a filter, washed with a small amount of water and dried.

Yd. : 75–80%
M.p. : 212°–215° C.

PREPARATION 3:
4-ISOPROPYLAMINOPYRIDINE-3-SULFONAMIDE 10 g of 4-chloropyridine-3-sulfonamide are dissolved in 50 cm$^3$ of methanol and 50 cm$^3$ of isopropylamine. The solution is introduced into a sealed tube and brought to 120° C. for 18 hours. After cooling, the reaction mixture is concentrated to dryness under vacuum (rotary evaporator) and the residue is taken up in 200 cm$^3$ of water. The precipitate corresponding to the title compound is collected on a filter and washed with water. The precipitate is redissolved in 100 cm$^3$ of dilute NaOH. The solution is decolored with charcoal, filtered and then acidified to a pH of 6.5–7. The crystalline precipitate obtained is collected on a filter, washed with water and dried.

Yd. : 45–50%
M.p. : 168°–171° C.

PREPARATIONS 4 AND 5:

These preparations are obtained according to the technique described in Eur. J. Med. Chem., (1980), Vol. 15, No. 4, pp 299–304.

PREPARATION 4:
4-CYCLOHEXYLAMINOPYRIDINE-3-SULFONAMIDE

PREPARATION 5:
4-CYCLOOCTYLAMINOPYRIDINE-3-SULFONAMIDE

PREPARATION 6:
2-AMINOPYRIDINE-3-SULFONAMIDE

Stage A : 2-Chloropyridine-3-sulfonamide 20 g of 3-amino-2-chloropyridine (commercial) are dissolved in 200 cm$^3$ of glacial acetic acid and 74 cm$^3$ of concentrated HCl. This solution is cooled in a bath of ice and salt to −10° C. and diazotized by progressive addition of 20 cm$^3$ of an aqueous solution containing 13 g of sodium nitrite.

Moreover, 8 g of CuCl$_2$ dissolved in 40 cm$^3$ of water and then the diazonium salt solution formed above are added to an acetic acid solution (320 cm$^3$) saturated with sulfur dioxide. After a few minutes, the suspension is concentrated to dryness and the residue is taken up in a water/ice mixture and then exhaustively extracted with diethyl ether.

The ethereal phase is dried over anhydrous MgSO$_4$, filtered and then concentrated under vacuum. The 2-chloropyridine-3-sulfonyl chloride residue is dissolved in 30 cm$^3$ of acetone and added progressively to 30 cm$^3$ of concentrated aqueous ammonia. After stirring for a few minutes, the mixture is concentrated to dryness on a rotary evaporator and the residue is taken up in 50 cm$^3$ of water. The precipitate is collected on a filter, washed with water and dried.

Yd. : 60–65%
M.p. : 185°–187° C.

Stage B: 2-Aminopyridine-3-sulfonamide

By carrying out the reaction as in Preparation 2, but replacing 4-chloropyridine-3-sulfonamide with the compound obtained in the preceding stage, 2-aminopyridine-3-sulfonamide is obtained.

Yd. : 75–80%
M.p. : 170°–172° C.

PREPARATION 7:
N-ISOPROPYL-4-AMINOPYRIDINE-3-SULFONAMIDE

Stage A: N-Isopropyl-4-chloropyridine-3-sulfonamide 7.5 g of 4-hydroxypyridine-3-sulfonic acid, 30 g of phosphorus pentachloride and 5 cm$^3$ of phosphorus oxychloride are brought to reflux for 5 hours. After cooling and concentrating under vacuum (rotary evaporator), the oily residue is poured onto ice and the aqueous phase is extracted 3 times with diethyl ether. The ethereal phase is dried over anhydrous MgSO$_4$, filtered and then concentrated under vacuum, and the 4-chloropyridine-3-sulfonyl chloride residue is dissolved in 20 cm$^3$ of dioxane and poured onto a solution of isopropylamine (2.6 cm$^3$) and triethylamine (5 cm$^3$) in dioxane (40 cm$^3$). After ½ hour at ambient temperature, the suspension obtained is concentrated under vacuum (rotary evaporator) to dryness. The residue is taken up in 100 cm$^3$ of water. After stirring for ½ hour, the crystalline precipitate obtained is collected on a filter, washed with water and dried.

Yd. : 50–55%
M.p. : 109°–111° C.

Stage B: N-Isopropyl-4-aminopyridine-3-sulfonamide

By carrying out the reaction as in Preparation 2, but starting from the compound obtained in the preceding stage, N-isopropyl-4-aminopyridine-3-sulfonamide is obtained.

Yd. : 70–75%
M.p. : 190°–193° C.

PREPARATION 8:
2-METHYLAMINOPYRIDINE-3-SULFONAMIDE 10 g of 2-chloropyridine-3-sulfonamide (obtained in Stage A of Preparation 6) are dissolved in 100 cm$^3$ of 40% aqueous methylamine solution and the solution is introduced into a sealed tube. The tube is placed at 150° C. for 18 hours. After cooling, the reaction mixture is concentrated under vacuum (rotary evaporator) to a volume of 30 cm$^3$. The crystalline precipitate corresponding to the title compound is collected on a filter, washed with water and dried.

Yd. : 80–85%
M.p. : 167°–169° C.

PREPARATION 9:
N-PENTYL-4-AMINOPYRIDINE-3-SULFONAMIDE

Stage A: N-Pentyl-4-chloropyridine-3-sulfonamide

By carrying out the reaction as in Stage A of Preparation 7, but replacing isopropylamine with 3.5 cm³ of pentylamine, the title compound (oil) is obtained.

Yd. : 50%

Stage B: N-pentyl-4-aminopyridine-3-sulfonamide

By carrying out the reaction as in Preparation 2, but starting from the compound obtained in the preceding stage, the title compound is obtained, which is purified by dissolving in 0.1N HCl, filtering the possible insoluble material, decoloring with absorbing charcoal and neutralizing the filtrate with dilute NaOH to a pH of 7.5. The precipitate obtained is collected on a filter, washed with water and dried.

Yd. : 30–35%

M.p. : 139°–142° C.

PREPARATION 10:
N-CYCLOHEXYL-4-AMINOPYRIDINE-3-SULFONAMIDE

By carrying out the reaction as in Preparation 7, but replacing isopropylamine with 3.4 cm³ of cyclohexylamine, the title compound is obtained.

Stage A: N-Cyclohexyl-4-chloropyridine-3-sulfonamide

Yd. : 50%

M.p. : 123°–125° C.

Stage B: N-Cyclohexyl-4-aminopyridine-3-sulfonamide

Yd. : 75–80%

M.p. : 197°–200° C.

PREPARATION 11:
N-PHENYL-4-AMINOPYRIDINE-3-SULFONAMIDE

By carrying out the reaction as in Preparation 9, but replacing pentylamine with 2.8 cm³ of aniline, the title compound is obtained.

Stage A: N-Phenyl-4-chloropyridine-3-sulfonamide

Yd. : 30–35%

M.p. : 178°–180° C.

Stage B: N-Phenyl-4-aminopyridine-3-sulfonamide

Yd. : 60–65%

M.p. : 231°–236° C.

PREPARATION 12:
N-METHYL-4-AMINOPYRIDINE-3-SULFONAMIDE

Stage A: N-Methyl-4-chloropyridine-3-sulfonamide 10 g of 4-hydroxypyridine-3-sulfonic acid, 30 g of phosphorus pentachloride and 5 cm³ of phosphorus oxychloride are brought to reflux for 5 hours.

After cooling and concentrating under vacuum (rotary evaporator), the oily residue is poured onto ice and the aqueous phase is extracted 3 times with diethyl ether. The ethereal phase is dried over anhydrous MgSO₄, filtered, then concentrated under vacuum and the 4-chloropyridine-3-sulfonyl chloride residue is dissolved in 20 cm³ of dioxane.

This solution is slowly poured onto 100 cm³ of 10% aqueous methylamine solution. The solution is concentrated under vacuum (rotary evaporator) to a volume of 40 cm³. The crystalline precipitate is collected on a filter, washed with water and dried.

Yd. : 70–75%

M.p. : 187°–190° C.

Stage B: N-Methyl-4-aminopyridine-3-sulfonamide

By carrying out the reaction as in Preparation 2, but starting from the compound obtained in the preceding stage, the title compound is obtained.

Yd. : 80–85%

M.p. : 168°–170° C.

PREPARATION 13:
4-METHYLAMINOPYRIDINE-3-SULFONAMIDE 10 g of 4-chloropyridine-3-sulfonamide are dissolved in 100 cm³ of 40% aqueous methylamine solution and the solution is introduced into a sealed tube. The tube is placed at 150° C. for 18 hours. After cooling, the reaction mixture is concentrated under vacuum (rotary evaporator) to a volume of 30 cm³. The crystalline precipitate corresponding to the title compound is collected on a filter, washed with water and dried.

Yd. : 85–90%

M.p. : 251°–254° C.

PREPARATION 14:
4-CHLORO-3-PYRIDYLSULFONYLGUANIDINE

4-Chloropyridine-3-sulfonyl chloride is prepared, from 5 g of 4-hydroxypyridine-3-sulfonic acid, according to the technique described in Preparation 12. This is dissolved in 100 cm³ of ether and then brought together with 25 cm³ of a 2N NaOH solution containing 4.25 g of guanidine carbonate (2 eq. of guanidine) with vigorous stirring. After reacting for one hour, the white precipitate corresponding to the title compound is collected on a filter, washed with water and dried.

Yd. : 15–20%

M.p. : 174°–177° C.

PREPARATION 15:
2,4-DICHLORO-5-PYRIDYLSULFONYLGUANIDINE

Stage A: 2,4-Dihydroxypyridine-5-sulfonic acid 5 g of 2,4-dihydroxypyridine are slowly added, at a temperature in the region of −10° C., to 12.5 cm³ of sulfuric oleum containing 20% SO₃ and containing 250 mg of HgSO₄. After having left to return to ordinary temperature, the mixture is progressively brought to 150° C. and then maintained at this temperature for 16 hours. The mixture is poured onto a MeOH/acetone (50/50) mixture cooled to around −50° C. A beige precipitate is formed which is recrystallized from the same MeOH/acetone mixture.

Yd. : 35–40%

M.p. : 297°–300° C.

Stage B: 2,4-Dichloro-5-pyridylsulfonylguanidine

By carrying out the reaction as in Preparation 14, but starting from the hydroxylated compound obtained in the preceding stage, the title compound is obtained.

M.p. : 202°–205° C.

PREPARATION 16:
2,6-DICHLORO-3-PYRIDYLSULFONYLGUANIDINE

Stage A: 3-Amino-2,6-dichloropyridine 4 g of 2,6-dichloro-3-nitropyridine are added to a suspension of 8 g of reduced iron in 200 cm³ of a water/alcohol (50/50) solution containing 1.6 g of NH₄Cl. The suspension is brought to reflux for 1 hour. The insoluble material is then removed by filtration. The filtrate is treated with 0.4 g of Na₂SO₃ and 0.4 g of NaH₂PO₂. The solution is adjusted to a pH of 8 and the alcohol is concentrated under reduced pressure until precipitation. The crystals corresponding to 3-amino-2,6- dichloropyridine are collected on a filter, washed with water and dried.

Yd. : 70%

M.p. : 121°–123° C.

Stage B: 2,6-Dichloro-3-pyridylsulfonylguanidine 2,6-Dichloropyridine-3-sulfonyl chloride is prepared from 10 g of 3-amino-2,6-dichloropyridine. The former is treated under the same conditions as during Preparation 14, in the presence of 8.5 g of guanidine carbonate.

Yd. : 30–35%

M.p. : 245°–250° C.

PREPARATION 17:
4-AMINO-3-CYCLOPENTYLCARBONYLAMINOSULFONYLPYRIDINE

Stage A: 4-Cyclopentylcarboxamido-3-cyclopentylcarbonylaminosulfonylpyridine

A mixture of 1 g of 4-aminopyridine-3-sulfonamide (Preparation 2), 2 cm³ of cyclopentanecarboxylic acid and 8 cm³ of phosphorus oxychloride is brought to reflux for 10 minutes. The reaction mixture is then concentrated under partial vacuum (rotary evaporator). The oily residue obtained is triturated with 100 cm³ of ice-cold water until a finely dispersed white precipitate is obtained. The precipitate is collected on a filter, washed with water and dried. It is purified by dissolving in the minimum amount of hot methanol, decoloring with absorbing charcoal, filtering and adding 2 volumes of water to the filtrate. After one night at +4° C., the crystals are collected on a filter, washed with water and dried.

Yd. : 80–85%
M.p. : 219°–222° C.

Stage B: 4-Amino-3-cyclopentylcarbonylaminosulfonylpyridine 1 g of 4-cyclopentylcarboxamido-3-cyclopentylcarbonylaminosulfonyl pyridine obtained in the preceding stage is dissolved in 20 cm³ of water containing 0.22 g of NaOH (2 equivalents). The solution is brought to reflux for 2 hours. The hot solution obtained is decolored with absorbing charcoal and filtered. The cooled filtrate is adjusted to a pH of 6 with 0.1N HCl. The precipitate obtained is collected on a filter, washed with water and dried.

Yd. : 80–85%
M.p. : 215°–217°–C.

PREPARATION 18:
4-AMINO-3-TRIFLUOROACETYLAMINOSULFONYLOPYRIDINE

A mixture of 1 g of 4-aminopyridine-3-sulfonamide (Preparation 2) and 7.5 cm³ of trifluoroacetic anhydride is brought to reflux for 4 hours. After cooling, the precipitate is filtered and washed with diethyl ether. The precipitate is resuspended in 25 cm³ of boiling methanol for 15 minutes. After cooling, the insoluble material corresponding to the title compound is collected on a filter, washed with methanol and then with diethyl ether and dried.

Yd. : 80–85%
M.p. : 262°–266° C.

PREPARATION 19 :
4-AMINO-5-ACETYLAMINOSULFONYL-2-CHLOROPYRIDINE

Stage A: 4-Amino-2-chloropyridine-5-sulfonamide

A solution of 1 g of 3-amino-6-chloro-4H- pyrido[4,3-e][1,2,4]thiadiazine 1,1-dioxide monohydrate (compound obtained in Example 31 below) in 30 cm³ of 50% v/v $H_2SO_4$ in water is brought to reflux for 15 minutes. After cooling, the solution is thinned down with 300 cm³ of ice-cold water and then neutralized to a pH of 7 using solid $NaHCO_3$. The white crystalline precipitate obtained is collected on a filter, washed with water and dried.

Yd. : 80%
M.p. : 240°–242° C.

Stage B: 4-Acetylamino-5-acetylaminosulfonyl-2-chloropyridine

A mixture of 1 g of 4-amino-2-chloropyridine-5- sulfonamide (obtained in the preceding stage) and 10 cm³ of acetic anhydride is brought to reflux for 15 minutes. After cooling, the crystals are collected on a filter, washed with acetic anhydride and then with diethyl ether and dried.

Yd. : 85–90%
M.p. : 219°–224° C.

Stage C: 4-Amino-5-acetylaminosulfonyl-2-chloropyridine

A solution of 0.5 g of 4-acetylamino-5-acetylaminosulfonyl-2-chloropyridine (preceding stage) in 10 cm³ of water containing 0.137 g of NaOH (2 equivalents) is brought to reflux for 15 minutes. After cooling, the solution is adjusted to a pH of 6 and the precipitate obtained is collected on a filter, washed with water and dried.

Yd. : 50–55%
M.p. : 235°–238° C.

PREPARATION 20:
2-AMINO-5-CHLOROPYRIDINE-3-SULFONAMIDE 2 g of 2-amino-5-chloropyridine are dissolved in 10 cm³ of chlorosulfonic acid maintained at −5° C. (ice+salt bath). The reaction mixture is progressively brought to ambient temperature and is then brought to reflux for 5 hours. After cooling, the solution is poured onto ice and the 2-amino-5-chloropyridine-3-sulfonyl chloride precipitate is filtered and washed with a small amount of cold water. The precipitate is dispersed with vigorous stirring in 50 cm³ of aqueous ammonia (10%). The title compound suspension obtained is then concentrated under vacuum to a volume of 20 cm³ and the crystalline precipitate is collected on a filter, washed with water and dried.

Yd. : 45–50%
M.p. : 215°–220° C.

PREPARATION 21:
4-ETHYLAMINOPYRIDINE-3-SULFONAMIDE

By carrying out the reaction as in Preparation 13, but starting from 2 g of 4-chloropyridine-3- sulfonamide and 20 cm³ of 70% ethylamine in water, the compound is obtained.

Yd. : 65–70%
M.p. : 192°–193° C.

PREPARATION 22:
4-PROPYLAMINOPYRIDINE-3-SULFONAMIDE 2 g of 4-chloropyridine-3-sulfonamide are dissolved in 10 cm³ of n-propylamine and 10 cm³ of isopropanol. The mixture is brought to reflux for 2 hours, the solution is then cooled and the solvent is evaporated. The solid obtained is redispersed in water (20 cm³). The insoluble material is collected on the filter, washed with water and dried.

Yd. : 90–95%
M.p. : 180°–181° C.

PREPARATION 23:
4-BUTYLAMINOPYRIDINE-3-SULFONAMIDE

The compound is obtained according to the technique described for Preparation 22, n-butylamine being used.

Yd. : 80–85%
M.p. : 143°–145° C.

PREPARATION 24:
4-(2',2',2'-TRIFLUOROETHYLAMINO)PYRIDINE-3-SULFONAMIDE

The compound is obtained according to the technique described for Preparation 13, using 50% v/v trifluoroethylamine in water.

Yd. : 35–40%
M.p. : 221°–222° C.

PREPARATION 25:
3-AMINO-5-METHYLPYRIDINE-2-SULFONAMIDE

Stage A: 2-Hydroxy-5-methyl-3-nitropyridine 25 g of 2-amino-5-methylpyridine are dissolved in 50 cm³ of concentrated sulfuric acid in a 600 cm³ round- bottomed flask. A mixture consisting of 40 cm³ of concentrated nitric acid and 40 cm³ of concentrated sulfuric acid is progressively added. The reaction mixture heats up with formation of foam. The temperature is maintained constant at 130° C. throughout the duration of the addition of the acid. The colored solution is then poured onto 300 g of ice and the pH is brought to around 3–4 by addition of aqueous ammonia. After standing in a refrigerator, the precipitate obtained is collected on a filter, washed with water and dried. It is recrystallized from hot water.

Yd. : 35–40%
M.p. : 243°–246° C.

Stage B: 2-Chloro-5-methyl-3-nitropyridine 5 g of 2-hydroxy-5-methyl-3-nitropyridine are dissolved in 32 cm³ of thionyl chloride to which 2 cm³ of N,N-dimethylformamide have been added. The mixture is then brought to reflux for 2 hours. After removing the solvent under partial vacuum, the product is distributed between distilled water (30 cm³) and chloroform (3×100 cm³). The chloroform fractions are combined, dried over $MgSO_4$, filtered and then concentrated under vacuum. The residue is recrystallized from ethanol/water. Yd.: 60–65%
M.p. : 48° C.

Stage C: 2-(5-Methyl-3-nitro-2-pyridyl)isothiourea hydrochloride

A solution of 23 g of 2-chloro-5-methyl-3-nitropyridine and 11.14 g of thiourea in 130 cm³ of ethanol is brought to reflux for 2 hours. After cooling and addition of 20 cm³ of petroleum ether (40°–60° C.), the precipitate obtained is collected on a filter, washed with petroleum ether and dried.
Yd. : 70–75%
M.p. : 205°–206° C.

Stage D: 2-Mercapto-5-methyl-3-nitropyridine

A solution of 19 g of isothiuronium salt in 110 cm³ of water is treated, with stirring, with 10.05 g of sodium carbonate and then with a solution of 7.59 g of NaOH in 10 cm³ of 1N HCl. The precipitate obtained is collected on a filter, washed with water and dried.
Yd. : 75–80%
M.p. : 198°–200° C.

Stage E: 5-Methyl-3-nitropyridine-2-sulfenamide

A solution of 12 g of 2-mercapto-5-methyl-3- nitropyridine and 28.6 g of triethylamine in 180 cm³ of dichloromethane is treated dropwise with 12 g of hydroxylamine-O-sulfonic acid dissolved in the minimum amount of water. At the end of the reaction, the solvent is removed under partial vacuum and the residue is taken up in 20 cm³ of water. The precipitate obtained is collected on a filter, washed with water and dried. It is recrystallized from a dichloromethane/petroleum jelly mixture.
Yd. : 90–95%
M.p. : 143°–145° C.

Stage F: 5-Methyl-3-nitropyridine-2-sulfonamide

A solution of 6 g of 5-methyl-3-nitropyridine-2- sulfenamide in 150 cm³ of acetonitrile is progressively treated with 2.5 g of potassium permanganate dissolved in the minimum amount of water. Completion of the reaction is assessed by thin layer chromatography. The black precipitate is removed by filtration and the filtrate is concentrated to a small volume. The solution is adjusted to a pH of 3 and the product is left to crystallize at 4° C. for 6 hours. The crystals are collected on a filter, washed with water and dried.
Yd. : 40–50%
M.p. : 160°–162° C.

Stage G: 3-Amino-5-methylpyridine-2-sulfonamide 3.46 g of reduced iron and 0.53 g of ammonium chloride are added to a solution of 2.17 g of 5-methyl-3- nitropyridine-2-sulfonamide in 60 cm³ of water/alcohol ($EtOH/H_2O$ : 1/1) solution. The mixture is brought to reflux for 20 minutes and then filtered while hot. The filtrate is concentrated to a small volume and left at 4° C. for 12 hours. The crystalline precipitate obtained is collected on a filter, washed with water and dried.
Yd. : 95–100%
M.p. : 192°–193° C.

The following examples illustrate the invention but do not limit it in any way.

EXAMPLE 1: 2,3-DIHYDRO-4H-PYRIDO[3,2-e][1,2,4]THIADIAZINE 1,1-DIOXIDE

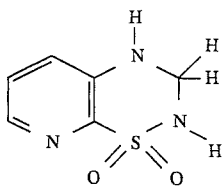

A mixture of 1 g of 3-aminopyridine-2-sulfonamide (Preparation 1) and 0.23 g of paraformaldehyde (1.3 eq.) in 10 cm³ of isopropanol to which 10 drops of ethyl acetate saturated with gaseous HCl have been added is brought to reflux for 1 to 2 hours. After cooling, the crystalline precipitate of the title compound is collected on a filter and washed with isopropanol. The product is recrystallized from hot water.
Yd. : 90%
M.p. : 242°–246° C.

EXAMPLE 2: 2,3-DIHYDRO-4H-PYRIDO[4,3-e][1,2,4]-THIADIAZINE 1,1-DIOXIDE

By carrying out the reaction as in Example 1 (except for the duration of the reflux which is from 2 to 4 hours), but replacing 3-aminopyridine-2-sulfonamide with 4-aminopyridine-3-sulfonamide (Preparation 2), the title compound is obtained.
Yd. : 70–75%
M.p. (monohydrate): 245°–248° C.

EXAMPLE 3: 4-ISOPROPYL-2,3-DIHYDRO-4H-PYRIDO[4,3-e]-[1,2,4]THIADIAZINE 1,1-DIOXIDE

A mixture of 1 g of 4-isopropylaminopyridine-3- sulfonamide (Preparation 3) and 1 g of paraformaldehyde in 20 cm³ of isopropanol to which 10 drops of ethyl acetate saturated with gaseous HCl have been added is brought to reflux for 3 hours. After cooling, the crystalline precipitate is filtered and washed with isopropanol. The precipitate is dissolved in 150 cm³ of hot methanol. The possible insoluble material is filtered. The filtrate is concentrated to dryness and the residue is taken up in 30 cm³ of water. The aqueous suspension is adjusted to a pH of 7–7.5 ($NaHCO_3$) and the precipitate corresponding to the title compound is filtered, washed with water and dried.
Yd. : 80–85%
M.p. : 202°–203° C.

EXAMPLE 4: 4-CYCLOHEXYL-2,3-DIHYDRO-4H-PYRIDO-[4,3-e][1,2,4]THIADIAZINE 1,1-DIOXIDE

By carrying out the reaction as in Example 3, but replacing Preparation 3 with Preparation 4, the title compound is obtained.
Yd. : 75–80%
M.p. : 247°–250° C.

EXAMPLE 5:
4-METHYL-2,3-DIHYDRO-4H-PYRIDO[4,3-e][1,2,4]THIADIAZINE 1,1-DIOXIDE

A mixture of 1 g of 4-methylaminopyridine-3-sulfonamide (Preparation 6) and 1 g of paraformaldehyde (excess) in 10 cm$^3$ of isopropanol to which 4 cm$^3$ of ethyl acetate saturated with gaseous HCl have been added is brought to reflux for 10 hours. After this lapse of time, the solvent is removed under partial vacuum (rotary evaporator) and the residue is redissolved in methanol. A possible insoluble material is filtered and the filtrate, to which 2 volumes of diethyl ether have been added, is left to precipitate the title compound in the form of crystals. The crystals are collected on a filter, washed with diethyl ether and dried. Yd. : 60-65%
M.p. (hydrochloride): 291-294° C.

EXAMPLE 6:
4-CYCLOOCTYL-2,3-DIHYDRO-4H-PYRIDO[4,3-e][1,2,4]THIADIAZINE 1,1-DIOXIDE

By carrying out the reaction as in Example 5, but replacing Preparation 6 with Preparation 5, the title compound is obtained. Yd. : 65-70% M.p. (hydrochloride): 254-255° C.

EXAMPLE 7:
2-ISOPROPYL-2,3-DIHYDRO-4H-PYRIDO[4,3-e][1,2,4]THIADIAZINE 1,1-DIOXIDE

A mixture of 0.5 g of N-isopropyl-4-aminopyridine-3-sulfonamide (Preparation 7) and 0.5 g of paraformaldehyde in 15 cm$^3$ of isopropanol to which 50 drops of ethyl acetate saturated with gaseous HCl have been added is brought to reflux for 24 hours. After this lapse of time, the solvent is removed under partial vacuum. The residue is redissolved in 20 cm$^3$ of methanol. The possible insoluble material is removed by filtration. The filtrate, treated with 40 cm$^3$ of water and stored for 2 hours at +4° C., produces a precipitate of the isopropoxymethylenated derivative of Preparation 7. It is collected on a filter, washed with water, dried and recrystallized from a CHCl$_3$/petroleum ether (40°-60° C.) (½) mixture. The dry product is introduced into an open round-bottomed flask and brought to a temperature of 180°-190° C. After 15 to 30 minutes, the molten mass solidifies. It is then cooled and then dissolved in a small volume of chloroform. The addition of 1 volume of petroleum ether (40°-60° C.) causes precipitation of crystals of the title compound. They are collected on a filter, washed with petroleum ether (40°-60° C.) and dried.

Yd. : 25-30%
M.p. : 209°-213° C.

EXAMPLE 8:
4-METHYL-2,3-DIHYDRO-4H-PYRIDO[2,3-e][1,2,4]THIADIAZINE 1,1-DIOXIDE

By carrying out the reaction as in Example 1, but using only 0.16 g of paraformaldehyde, maintaining reflux for 24 hours and recrystallizing from a MeOH/H$_2$O (⅓) mixture, the title compound is obtained by replacing Preparation 1 with Preparation 8.

Yd. : 75-80%
M.p. : 184°-187° C.

EXAMPLE 9:
2-PENTYL-2,3-DIHYDRO-4H-PYRIDO[4,3-e][1,2,4]THIADIAZINE 1,1-DIOXIDE

A mixture of 0.5 g of N-pentyl-4-aminopyridine-3-sulfonamide (Preparation 9) and 0.5 g of paraformaldehyde in 15 cm$^3$ of isopropanol to which 50 drops of ethyl acetate saturated with gaseous HCl have been added is brought to reflux for 48 hours. After this lapse of time, the solvent is removed under partial vacuum. The residue is suspended in 20 cm$^3$ of 0.1N NaOH. After stirring for 1 hour at ambient temperature, the insoluble material is collected on a filter, washed with water and recrystallized twice from a methanol/water (½) mixture and then once from CHCl$_3$/petroleum ether (40°-60° C.) (1/1).

Yd. : 30-35%
M.p. : 188°-192° C.

EXAMPLE 10:
2-CYCLOHEXYL-2,3-DIHYDRO-4H-PYRIDO[4,3-e][1,2,4]THIADIAZINE 1,1-DIOXIDE

By carrying out the reaction as in Example 7, but replacing Preparation 7 with Preparation 10, the title compound is obtained.

M.p. : 173° C.

EXAMPLE 11:
2-PHENYL-2,3-DIHYDRO-4H-PYRIDO[4,3-e][1,2,4]THIADIAZINE 1,1-DIOXIDE

By carrying out the reaction as in Example 9, but replacing Preparation 9 with Preparation 11, the title compound is obtained.

Yd. : 30-35%
M.p. : 225°-230° C.

EXAMPLE 12:
3-METHYL-2,3-DIHYDRO-4H-PYRIDO[3,2-e][1,2,4]THIADIAZINE 1,1-DIOXIDE

A mixture of 1 g of 3-aminopyridine-2-sulfonamide (Preparation 1) and 0.28 g of acetaldehyde in 10 cm$^3$ of isopropanol to which 10 drops of ethyl acetate saturated with gaseous HCl have been added is brought to reflux for 1 to 2 hours. After cooling, a crystalline precipitate of the title compound is collected on a filter and washed with isopropanol. The 3-methyl-2,3-dihydro-4H-pyrido[3,2-e][1,2,4]thiadiazine 1,1-dioxide is recrystallized from a CH$_3$OH/H$_2$O (¼) mixture.

Yd. : 90%
M.p. : 204°-209° C.

EXAMPLE 13:
3-METHYL-2,3-DIHYDRO-4H-PYRIDO[4,3-e]-[1,2,4]THIADIAZINE 1,1-DIOXIDE

By carrying out the reaction as in Example 12, but replacing Preparation 1 with Preparation 2, the title compound is obtained.

Yd. : 70-75%
M.p. (monohydrate): 229°-231° C.

EXAMPLE 14:
2,3-DIMETHYL-2,3-DIHYDRO-4H-PYRIDO[4,3-e][1,2,4]THIADIAZINE 1,1-DIOXIDE 1 g of N-methyl-4-aminopyridine-3-sulfonamide (Preparation 12) is brought to reflux for 6 hours in a mixture of 8 cm³ of isopropanol, 32 cm³ of acetaldehyde and 6 cm³ of ethyl acetate saturated with gaseous HCl. After this lapse of time, the reaction mixture is concentrated under partial vacuum (rotary evaporator). The oily mass obtained is dissolved and adjusted to a pH of 7 with NaHCO₃. The aqueous suspension is extracted 3 times with 100 cm³ of dichloromethane. The organic phase is dried (MgSO₄), filtered and concentrated to dryness. The residue obtained is dissolved in 10 cm³ of methanol, and then 10 cm³ of ethyl acetate saturated with gaseous HCl are added. The addition of 60 cm³ of diethyl ether causes the precipitation of crystals corresponding to the title compound. They are collected on a filter, washed with diethyl ether and dried.

Yd. : 60–65%

M.p. (hydrochloride): 252°–255° C.

EXAMPLE 15: 2,3-DIHYDRO-4H-PYRIDO[2,3-e][1,2,4]THIADIAZINE 1,1-DIOXIDE

Stage A: 4H-Pyrido[2,3-e][1,2,4]thiadiazine 1,1-dioxide

A mixture of 2 g of 2-aminopyridine-3-sulfonamide (Preparation 6) and 20 cm³ of ethyl orthoformate is brought to reflux for 1 hour. After cooling, the crystalline precipitate obtained is collected on a filter and washed with ether.

Yd. : 90–95%

M.p. : 298°–301° C.

Stage B: 2,3-Dihydro-4H-pyrido[2,3-e][1,2,4thiadiazine 1,1-dioxide 1 g of 4H-pyrido[2,3-e][1,2,4]thiadiazine 1,1- dioxide is suspended in 30 cm³ of water. A solution of 0.83 g of NaBH₄ in 5 cm³ of water is added to the suspension. After stirring for 15 minutes at ambient temperature, the pH of the solution is adjusted to 6.5–7 using dilute HCl. The precipitate obtained is filtered, washed with water and dried. The dried compound is dissolved in 200 cm³ of dichloromethane. The possible insoluble material is removed by filtration. The filtrate is treated with an equal volume of petroleum ether (40°–60° C.) and placed at +4° C. overnight. The crystals obtained are collected on a filter and dried.

Yd. : 75–80%

M.p. : 178°–179° C.

EXAMPLE 16:
4H-PYRIDO[3,2-e][1,2,4]THIADIAZINE 1,1-DIOXIDE

By carrying out the reaction as in Stage A of Example 15, but using Preparation 1, the title compound is obtained.

Yd. : 85–90%

M.p. : 320°–325° C.

EXAMPLE 17:
3-METHYL-4H-PYRIDO[3,2-e][1,2,4]THIADIAZINE 1,1-DIOXIDE 1 g of 3-aminopyridine-2-sulfonamide (Preparation 1) and 1 g of p-toluenesulfonic acid are dissolved in 6 cm³ of ethyl orthoacetate. After 10 minutes at room temperature, the precipitate obtained is collected on a filter, washed with diethyl ether and dried. It is recrystallized from hot water.

Yd. : 80–85%

M.p. : 263°–266° C.

EXAMPLE 18:
4H-PYRIDO[4,3-e][1,2,4]THIADIAZINE 1,1-DIOXIDE 3.3 cm³ of formic acid and 6.6 cm³ of acetic anhydride are kept stirring at 50° C. for 15 minutes. 1 g of 4-aminopyridine-3-sulfonamide (Preparation 2) is added to this solution and the reaction mixture is brought to reflux for 2 hours. After cooling, the crystals obtained are collected on a filter, washed with a small amount of acetic acid and then with diethyl ether and dried.

Yd. : 75–80%

M.p. : 296°–298° C.

EXAMPLE 19: 2-ISOPROPYL-2H-PYRIDO[4,3-e][1,2,4]THIADIAZINE 1,1-DIOXIDE

A mixture of 0.5 g of N-isopropyl-4- aminopyridine-3-sulfonamide (Preparation 7) and 5 cm³ of ethyl orthoformate is maintained in an open vessel at 120° C. for 4 hours. After concentrating the solution under partial vacuum, the oily residue obtained is triturated with 10 cm³ of ice-cold water. The crystalline precipitate which appears is collected on a filter and washed with water. It is recrystallized from a methanol/water (½) mixture.

Yd. : 80–85%

M.p. : 175°–178° C.

EXAMPLE 20:
3-METHYL-4H-PYRIDO[4,3-e][1,2,4]THIADIAZINE 1,1-DIOXIDE 1 g of 4-aminopyridine-3-sulfonamide (Preparation 2) is maintained for 4–6 hours at reflux in 10 cm³ of acetic anhydride. After cooling, the reaction mixture is treated with 60 cm³ of diethyl ether. The precipitate obtained is filtered, washed with diethyl ether and dried. It is recrystallized from hot water.

Yd. : 70–75%

M.p. (monohydrate): 264°–268° C.

EXAMPLE 21:
3-ETHYL-4H-PYRIDO[4,3-e][1,2,4]THIADIAZINE 1,1-DIOXIDE

A mixture of 1 g of 4-aminopyridine-3-sulfonamide (Preparation 2) and 10 cm³ of propionic anhydride is heated at 150° C. for 8 hours. After cooling, an equal volume of diethyl ether is added and the precipitate obtained is collected on a filter, washed with diethyl ether and dried. It is recrystallized from hot water.

Yd. : 45–50%

M.p. (monohydrate): 220°–223° C.

EXAMPLE 22:
3-PROPYL-4H-PYRIDO[4,3-e][1,2,4]THIADIAZINE 1,1-DIOXIDE MONOHYDRATE

A mixture of 1 g of 4-aminopyridine-3-sulfonamide (Preparation 2) and 10 cm³ of butyric anhydride is heated to 180° C. for 18 hours. After cooling, the crystals obtained are collected on a filter, washed with a small amount of butyric anhydride and with diethyl ether and then dried. The product is recrystallized from hot water.

Yd. : 50–55%

M.p. (monohydrate) : 210°–212° C.

EXAMPLE 23: 3-ISOPROPYL-4H-PYRIDO[4,3-e][1,2,4]THIADIAZINE 1,1-DIOXIDE

A mixture of 1 g of 4-aminopyridine-3-sulfonamide (Preparation 2) and 10 cm³ of isobutyric anhydride is maintained at 170° C. for 72 hours. After cooling, the precipitate obtained is filtered, washed with diethyl ether and dried. The product is dissolved while hot in the minimum amount of methanol. The hot solution is decolored with absorbing charcoal, filtered and then treated with 3 volumes of water. After standing overnight at +4° C., the crystals obtained are collected on a filter, washed with water and dried.

Yd. : 40–45%

M.p. : 248°–250° C.

EXAMPLE 24: 3-TERT-BUTYL-4H-PYRIDO[4,3-e][1,2,4]THIADIAZINE 1,1-DIOXIDE

The title compound is obtained from 4- aminopyridine-3-sulfonamide (Preparation 2) and trimethylacetic anhydride by applying the experimental conditions described for Example 23.

Yd. : 40–45%

M.p. : 290°–293° C.

EXAMPLE 25: 3,4-DIMETHYL-4H-PYRIDO[4,3-e][1,2,4]THIADIAZINE 1,1-DIOXIDE

A mixture of 1 g of 4-methylaminopyridine-3- sulfonamide (Preparation 13) and 10 cm³ of acetic anhydride is brought to reflux for 4 hours. After cooling, the reaction mixture is treated with an equal volume of diethyl ether with stirring. The crystalline precipitate is filtered, washed with diethyl ether and dried. It is purified by dissolving in the minimum amount of hot methanol and adding 2 volumes of water. After standing at +4° C., the crystals obtained are collected on a filter, washed with water and dried.

Yd. : 80–85%

M.p. : 227°–228° C.

EXAMPLE 26: 4-ISOPROPYL-3-METHYL-4H-PYRIDO[4,3-e][1,2,4]THIADIAZINE 1,1-DIOXIDE

The title compound is obtained from 4-isopropylaminopyridine-3-sulfonamide (Preparation 3) by applying the experimental conditions described for Example 25.

Yd. : 70%

M.p. : 196°–197° C.

EXAMPLE 27: 4-CYCLOHEXYL-3-METHYL-4H-PYRIDO[4,3-e][1,2,4]THIADIAZINE 1,1-DIOXIDE

The title compound is obtained from 4- cyclohexylaminopyridine-3-sulfonamide (Preparation 4) by applying the experimental conditions described for Example 25.

Yd. : 60–65%

M.p. : 224°–226° C.

EXAMPLE 28: 4-CYCLOOCTYL-3-METHYL-4H-PYRIDO[4,3-e][1,2,4]THIADIAZINE 1,1-DIOXIDE

The title compound is obtained from 4- cyclooctylaminopyridine-3-sulfonamide (Preparation 5) by applying the experimental conditions described for Example 25.

Yd. : 60–65%

M.p. : 207°–210° C.

EXAMPLE 29: 2-CYCLOHEXYL-4H-PYRIDO[4,3-e][1,2,4]THIADIAZINE 1,1-DIOXIDE

The title compound is obtained from N- cyclohexyl-4-aminopyridine-3-sulfonamide (Preparation 10) by applying the experimental conditions described for Example 19.

Yd. : 80–85%

M.p. : 144°–147° C.

EXAMPLE 30: 3-AMINO-4H-PYRIDO[4,3-e][1,2,4]THIADIAZINE 1,1-DIOXIDE

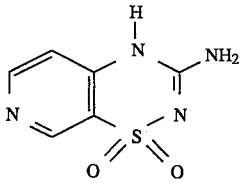

A mixture 0.25 g of 4-chloro-3-pyridylsulfonylguanidine (Preparation 14) and 0.25 g of potassium carbonate in 5 cm³ of dioxane/DMF (80/20) is heated at reflux for 24 hours. After cooling, the white precipitate obtained is filtered and then redissolved in the minimum amount of water. The solution is adjusted to a pH of 7 and the white precipitate corresponding to the title compound is collected on a filter, washed with water and dried.

Yd. : 40–45%

M.p. (monohydrate): 327°–330° C.

EXAMPLE 31: 3-AMINO-6-CHLORO-4H-PYRIDO[4,3-e][1,2,4]THIADIAZINE 1,1-DIOXIDE

By carrying out the reaction as in Example 30, but starting from Preparation 15, the title compound is obtained.

Yd. : 40–45%

M.p. (monohydrate): 316°–319° C.

EXAMPLE 32: 3-AMINO-6-CHLORO-4H-PYRIDO[2,3-e][1,2,4]THIADIAZINE 1,1-DIOXIDE

The title compound is obtained from Preparation 16 according to the technique described for Example 30.

Yd. : 75%

M.p. (monohydrate): 327°–330° C.

EXAMPLE 33: 3-CYCLOPENTYL-4H-PYRIDO[4,3-e][1,2,4]THIADIAZINE 1,1-DIOXIDE

A solution of 1 g of 4-amino-3-cyclopentylcarbonylaminosulfonylpyridine (Preparation 17) in 1 cm³ of DMF and 10 cm³ of phosphorus oxychloride is stirred at ambient temperature for 3 hours. The solvents are removed under partial vacuum (rotary evaporator) and the residue is dissolved in 10 cm³ of water. The solution is adjusted to a pH of 4 (NaHCO₃) and the crystalline precipitate obtained is collected on a filter, washed with water and dried.

Yd. : 15–20%

M.p. : 263°–266° C.

EXAMPLE 34:
3-TRIFLUOROMETHYL-4H-PYRIDO[4,3-e] [1,2,4]THIADIAZINE 1,1-DIOXIDE

A mixture of 1 g of 4-amino-3-trifluoroacetylaminosulfonylpyridine (Preparation 18) and 20 cm³ of phosphorus oxychloride is brought to reflux for 18 hours. The solvent is removed under partial vacuum and the oil obtained, triturated with 5 ml of ice-cold water, produces a precipitate. The latter is collected on a filter, washed with water and dried. It is then purified by dissolving in the minimum amount of methanol and then adding 3 volumes of diethyl ether and 3 volumes of petroleum ether (40°–60° ). The crystals obtained are collected on a filter, washed with diethyl ether and dried.

Yd. : 60–65%

M.p. (monohydrate) : 236°–240° C.

EXAMPLE 35:
6-CHLORO-3-METHYL-4H-PYRIDO[4,3-e] [1,2,4]THIADIAZINE 1,1-DIOXIDE 0.2 g of 4-amino-5-acetylaminosulfonyl-2- chloropyridine (Preparation 19) is introduced into an open round-bottomed flask placed on an oil bath at 240° C. The temperature of the oil bath is brought over a period of a half-hour from 240° C. to 270° C. The molten mass is then cooled. It is dissolved in 4 cm³ of a tepid NaHCO₃ solution (2% m/v). The solution is decolored with absorbing charcoal, filtered and then adjusted to a pH of 4 using formic acid. The crystalline precipitate obtained is collected on a filter, washed with water and dried.

Yd. : 40%

M.p. (monohydrate) : 309°–312° C.

EXAMPLE 36:
7-CHLORO-3-METHYL-4H-PYRIDO[2,3-e] [1,2,4]THIADIAZINE 1,1-DIOXIDE

A mixture of 1 g of 2-amino-5-chloropyridine-3- sulfonamide (Preparation 20) and 10 cm³ of acetic anhydride is brought to reflux for 6 hours. After cooling, the crystals are filtered off, washed with a small amount of acetic anhydride and then with diethyl ether and dried. The crystals are redissolved in 50 cm³ of 0.1N NaOH. The possible insoluble material is removed by filtration. The filtrate, adjusted to a pH of 4 using formic acid, allows crystals to precipitate. They are collected on a filter, washed with water and dried.

Yd. : 60–65%

M.p. : >340° C.

EXAMPLE 37:
3-ISOPROPOXY-4H-PYRIDO[3,2-e][1,2,4] THIADIAZINE 1,1-DIOXIDE

Stage A : 3-Oxo-2,3-dihydro-4H-pyrido[3,2-e][1,2,4]thiadiazine 1,1-dioxide

An intimate mixture of 5 g of 3-aminopyridine-2- sulfonamide (Preparation 1) and 1.91 g of urea is progressively brought to a temperature of 200° C. (melting). After gas has ceased to be given off and the mass has solidified, the reaction mixture is cooled to ambient temperature. The solid mass is redissolved in 1N NaOH and the solution obtained, optionally decolored with absorbing charcoal, is then adjusted to a pH of 2 using 1N HCl. The white precipitate corresponding to the title compound is collected on a filter, washed with water and dried.

Yd. : 85–90%

M.p. : >300° C.

Stage B: 3-Isopropoxy-4H-pyrido[3,2-e][1,2,4]thiadiazine 1,1-dioxide

The sodium salt of 3-oxo-2,3-dihydro-4H- pyrido[3,2e] [1,2,4]thiadiazine 1,1-dioxide (0.5 g) obtained in the preceding stage is prepared in methanol solution (7 cm³) by reacting with 1.1 equivalents of NaOH (0.11 g). After removal of the solvent under partial vacuum, the solid salt is redissolved in 5 cm³ of DMF and then treated with 0.4 cm³ of isopropyl iodide. After reacting for 7 hours at ambient temperature, the solvent is removed under partial vacuum and the residue is taken up in 15 cm³ of water. The aqueous suspension is adjusted to a pH of 12 with 2N NaOH. The insoluble material, consisting of 2-isopropyl-3-oxo-2, 3-dihydro-4H-pyrido[3,2-e][1,2,4] thiadiazine 1,1-dioxide (M.p.: 218°–221° C.), is removed by filtration. The filtrate is adjusted to a pH of 2 using 1N HCl. The precipitate corresponding to the title compound is collected on a filter, washed with water and dried.

M.p.: 196°–199° C.

EXAMPLE 38:
3-THIOXO-2,3-DIHYDRO-4H-PYRIDO[4,3-e][1,2,4]-THIADIAZINE 1,1-DIOXIDE

Stage A: 3-Oxo-2,3-dihydro-4H-pyrido[4,3-e][1,2,4]thiadiazine 1,1-dioxide

The title compound is obtained from 4-amino- pyridine-3-sulfonamide (Preparation 2) by applying the experimental conditions described for Example 37.

Yd. : 85–90%

M.p. (monohydrate): >330° C.

Stage B: 3-Thioxo-2,3-dihydro-4H-pyrido[4,3-e][1,2,4]thiadiazine 1,1-dioxide

A mixture of 3 g of 3-oxo-2,3-dihydro-4H- pyrido[4,3e] [1,2,4]thiadiazine 1,1-dioxide obtained in the preceding stage and 5.022 g of P₂S₅ in 30 cm³ of anhydrous pyridine is brought to reflux for 24 hours. The reaction mixture is then concentrated under partial vacuum (rotary evaporator). The residue is dissolved in the minimum amount of 2N NaOH. The solution obtained is treated with active charcoal, filtered and then adjusted to a pH of 2 using 1N HCl. The precipitate is collected on a filter and washed with H₂O. It is redissolved in an aqueous NaHCO₃ solution (2.5% m/v), treated with active charcoal and reprecipitated at a pH of 2 using 1N HCl.

Yd.: 45–50%

M.p. (monohydrate): 292°–294° C.

EXAMPLE 39:
3-METHYLTHIO-4H-PYRIDO[4,3-e][1,2,4]-THIADIAZINE 1,1-DIOXIDE

First process:

5.5 g of 3-thioxo-2,3-dihydro-4H-pyrido[4,3-e] [1,2,4] thiadiazine 1,1-dioxide (obtained in Example 38) are dissolved in 165 cm³ of water containing 4 g of NaHCO₃. 120 cm³ of methanol and then 8 cm³ of methyl iodide are added to this solution. After stirring for 1 hour at ambient temperature, the reaction mixture is concentrated to a volume of 150 cm³ (rotary evaporator) and then adjusted to a pH of 2–3. The precipitate obtained is collected on a filter, washed with water and dried.

Yd.: 65–70%

M.p. (monohydrate): 242°–245° C.

Second process:

1.2 cm³ of dimethyl sulfate are added to a solution of 1 g of 3-thioxo-2,3-dihydro-4H-pyrido[4,3 -e] [1,2,4]thiadiazine 1,1-dioxide in 10 cm³ of anhydrous DMF. After several hours at ambient temperature, the solvent is removed under partial vacuum and the residue is redissolved in the minimum amount of 1N NaOH. The solution, decolored with absorbing charcoal and filtered, is adjusted to a pH of 7 using 0.1N HCl. The white precipitate corresponding to the title compound is collected on a filter, washed with water and dried.

Yd.: 80–85%

EXAMPLE 40:
3-ISOPROPYLAMINO-4H-PYRIDO[4,3-e][1,2,4]-THIADIAZINE 1,1-DIOXIDE

A solution of 0.7 g of 3-methylthio-4H-pyrido[4,3-e][1,2,4]thiadiazine 1,1-dioxide obtained in Example 39 in 7 cm³ of isopropylamine is maintained in a sealed tube at 150° C. for 4 hours. After cooling, the solution is concentrated to dryness, the residue is taken up in 10 cm³ of water and the pH is adjusted to the value of 7. The precipitate obtained is collected on a filter, washed with water and recrystallized from hot water.

Yd.: 75%

M.p. (monohydrate): 197°–200° C.

EXAMPLE 42:
3-PROPYLAMINO-4H-PYRIDO[4,3-e ]-[1,2,4 ]THIADIAZINE 1,1-DIOXIDE MONOHYDRATE

By carrying out the reaction as in Example 40, but replacing isopropylamine with propylamine, the title compound is obtained.

Yd.: 75–80%

M.p.: 194°–197° C.

EXAMPLE 42 TO 44:

By carrying out the reaction as in Example 40, but replacing isopropylamine with the appropriate amine, the following title compounds are obtained:

EXAMPLE 42:
3-BUTYLAMINO-4H-PYRIDO[4,3-e][1,2,4]-THIADIAZINE 1,1-DIOXIDE

Yd. : 80–85%

M.p.: 167°–170° C.

EXAMPLE 43:
3-(2-METHYLPROPYL)AMINO-4H-PYRIDO-[4,3-e ][1,2,4]THIADIAZINE 1,1-DIOXIDE

Yd.: 75–80%

M.p.: 221°–224° C.

EXAMPLE 44:
3-(1-METHYLPROPYL)AMINO-4H-PYRIDO-[4,3-e ] [1,2,4]THIADIAZINE 1,1-DIOXIDE

Yd.: 75–80%

M.p. (monohydrate): 212°–215° C.

EXAMPLE 45:
3-(1,2-DIMETHYLPROPYL)AMINO-4H-PYRIDO-[4,3-e][1,2,4]THIADIAZINE 1,1-DIOXIDE

A solution of 0.8 g of 3-methylthio-4H-pyrido[4,3e][1,2,4]thiadiazine 1,1-dioxide obtained in Example 39 in 8 cm³ of 1,2-dimethylpropylamine is brought to reflux for 2 days. After removing the solvent under partial vacuum, the residue is taken up in 10 cm³ of water and the pH is adjusted to 7. The aqueous suspension is extracted with three $CHCl_3$ fractions. The organic phase is dried ($MgSO_4$) and concentrated to dryness under partial vacuum. The oil obtained, taken up in a small volume of ethyl acetate and placed overnight at +4° C., produces a precipitate of the title compound. It is collected on a filter, washed with petroleum ether (40°–60° C.) and dried.

Yd. : 80–85%

M.p. : 199°–202° C.

EXAMPLE 46:
3-CYCLOHEXYLAMINO-4H-PYRIDO[4,3-e]-[1,2,4]THIADIAZINE 1,1-DIOXIDE

A solution of 0.7 g of 3-methylthio-4H- pyrido[4,3-e] [1,2,4]thiadiazine 1,1-dioxide in 7 cm³ of cyclohexylamine is heated at reflux for 4 hours. The reaction mixture is concentrated under partial vacuum and the residue is taken up in 10 cm³ of water and is slightly basified by addition of 10% sodium hydroxide solution. The aqueous phase is stirred with 25 cm³ of diethyl ether in order to extract a possible excess of cyclohexylamine. After separation by settling, the aqueous solution is adjusted to a pH of 7 and the white precipitate is collected on a filter and washed with water. It is recrystallized from hot water.

Yd.: 90–95%

M.p. (monohydrate): 134°–137° C.

EXAMPLES 47 AND 48

By carrying out the reaction as in Example 46, but using the appropriate amines, the compounds of the following examples are obtained:

EXAMPLE 47:
3-CYCLOPENTYLAMINO-4H-PYRIDO[4,3-e]-[1,2,4]THIADIAZINE 1,1-DIOXIDE

Yd. : 90–95%

M.p. (monohydrate): 237°–240° C.

EXAMPLE 48:
3-(4-MORPHOLINYL)AMINO-4H-PYRIDO[4,3-e]-[1,2,4]THIADIAZINE 1,1-DIOXIDE

Yd. : 70–75%

M.p. (monohydrate): 291°–293° C.

EXAMPLE 49:
6-CHLORO-2,3-DIHYDRO-4H-PYRIDO[4,3-e]-[1,2,4]THIADIAZINE 1,1-DIOXIDE

The title compound is obtained from 4-amino-2- chloropyridine-5-sulfonamide (obtained in Stage A of Preparation 19) under the experimental conditions described for Example 1.

Yd. : 65%

M.p. : 202°–206° C.

EXAMPLE 50:
3-AMINO-4H-PYRIDO[3,2-e][1,2,4]THIADIAZINE 1,1-DIOXIDE

An intimate mixture of 1 g of 3-aminopyridine-2- sulfonamide (Preparation 1) and 2.1 g of guanidine carbonate is progressively brought to the molten state (200° C.) and then heated for 24 hours at this temperature. After cooling, the residue is taken up in water. The possible insoluble material is filtered and the filtrate, treated with animal charcoal, is acidified to a pH of 7. The white precipitate is collected on a filter, washed with water and recrystallized from hot water.

Yd. : 35–40%

M.p. (monohydrate): >330° C.

EXAMPLE 51:
3-ETHYL-2,3-DIHYDRO-4H-PYRIDO[4,3-e]-[1,2,4]THIADIAZINE 1,1-DIOXIDE 0.5 g of 4-aminopyridine-3-sulfonamide (Preparation 2) and 0.34 g (2 equivalents) of propionaldehyde are introduced into 5 cm$^3$ of isopropanol to which 10 drops of a saturated solution of hydrochloric acid in ethyl acetate have been added. After refluxing for 2 h, the solution obtained is concentrated to dryness and the residue is recrystallized from a ⅓ isopropanol/petroleum ether (40°–60° C.) mixture.

Yd. : 75–80%

M.p. : 215°–217° C.

EXAMPLE 52:
3-PROPYL-2,3-DIHYDRO-4H-PYRIDO[4,3-e]-[1,2,4]THIADIAZINE 1,1-DIOXIDE

By carrying out the reaction as in Example 51, but replacing propionaldehyde with butyraldehyde, the title compound is obtained. However, after refluxing for 2 h, the crystal suspension obtained is cooled. The crystals are collected on a filter, washed with isopropanol, dried and recrystallized from a ½ methanol/diethyl ether mixture.

Yd. : 70–75%

M.p. : 229°–234° C.

EXAMPLES 53 TO 56:

By carrying out the reaction as in Example 52, but replacing butyraldehyde with the appropriate aldehyde, the compounds of the following examples are obtained:

EXAMPLE 53:
3-ISOPROPYL-2,3-DIHYDRO-4H-PYRIDO[4,3-e][1,2,4]THIADIAZINE 1,1-DIOXIDE

Yd. : 75–80%

M.p. : 250°–254° C.

EXAMPLE 54:
3-ETHYLPROPYL-2,3-DIHYDRO-4H-PYRIDO-[4,3-e][1,2,4 ]THIADIAZINE 1,1-DIOXIDE

Yd. : 75–80%

M.p. : 224°–226° C.

EXAMPLE 55:
3-CYCLOHEXYL-2,3-DIHYDRO-4H-PYRIDO[4,3-e][1,2,4]THIADIAZINE 1,1-DIOXIDE

Recrystallization solvent: ½ methanol/water.

Yd. : 75–80%

M.p. : 272°–276° C.

EXAMPLE 56:
3-PHENYL-2,3-DIHYDRO-4H-PYRIDO[4,3-e]-[1,2,4]THIADIAZINE 1,1-DIOXIDE

Recrystallization solvent: ⅓ isopropanol/petroleum ether (40°–60° C.).

Yd. : 70–75%

M.p. : 214°–216° C.

EXAMPLE 57:
3-CHLOROMETHYL-2,3-DIHYDRO-4H-PYRIDO[4,3-e] [1,2,4]THIADIAZINE 1,1-DIOXIDE

Yd. : 70–75%

M.p. (hydrochloride): 264°–267° C.

EXAMPLE 58:
2-METHYL-2,3-DIHYDRO-4H-PYRIDO[4,3-e][1,2,4]THIADIAZINE 1,1-DIOXIDE

The title compound is obtained from N-methyl-4- aminopyridine-3sulfonamide (Preparation 12) by applying the experimental conditions described for Example 9. However, after refluxing for 24 hours, the solvent is removed under partial vacuum. The residue is purified on a silica column, using a 95/5 chloroform/methanol mixture as eluent phase. The compound collected is then recrystallized from a 4/1 chloroform/methanol mixture.

Yd. : 40–45%

M.p. : 209°–211° C.

EXAMPLE 59:
4-ETHYL-2,3-DIHYDRO-4H-PYRIDO[4,3-e]-[1,2,4]THIADIAZINE 1,1-DIOXIDE

The compound of Example 59 is obtained from 4- ethylaminopyridine-3-sulfonamide (Preparation 21) by applying the experimental conditions described in Example 3.

Yd. : 90–95%

M.p. : 229°–230° C.

EXAMPLE 60:
4-PROPYL-2,3-DIHYDRO-4H-PYRIDO[4,3-e]-[1,2,4]THIADIAZINE 1,1-DIOXIDE

The compound of Example 60 is obtained from 4-propylaminopyridine-3-sulfonamide (Preparation 22) by applying the experimental conditions described in Example 3.

Yd. : 75–80%

M.p. : 160°–163° C.

EXAMPLE 61:
4-BUTYL-2,3-DIHYDRO-4H-PYRIDO[4,3-e]-[1,2,4]THIADIAZINE 1,1-DIOXIDE

The compound is obtained from 4-butylamino- pyridine-3-sulfonamide by applying the experimental conditions described for Example 3. The corresponding hydrochloride is obtained by dissolving the base compound in ethyl acetate and by adding a saturated solution of hydrochloric acid in ethyl acetate. The hydrochloride precipitates. It is collected on a filter, washed with ethyl acetate and dried.

Yd. : 65–70%

M.p. : 277°–280° C. (hydrochloride)

EXAMPLE 62:
4-(2',2',2'-TRIFLUOROETHYL)-2,3-DIHYDRO-4H-PYRIDO[4,3-e][1,2,4]THIADIAZINE 1,1-DIOXIDE

The compound is obtained from 4-(2',2',2'-trifluoroethylamino)pyridine-3-sulfonamide (Preparation 24) by applying the experimental conditions described in Example 3.

Yd. : 70–75%

M.p. : 200°–201° C.

EXAMPLE 63:
4-METHYL-4H-PYRIDO[3,2-e][1,2,4]THIADIAZINE 1,1-DIOXIDE 1.2 g of potassium carbonate and 1.37 g of iodomethane are added to a solution of 0.6 g of 4H- pyrido[3,2-e][1,2,4] thiadiazine 1,1-dioxide (Example 16) in 15 cm³ of acetonitrile. The suspension is heated at 50° C. for 3 hours. The acetonitrile is then removed by evaporation under partial vacuum. The residue is taken up in 20 cm³ of water. The title product, which has little solubility in water, is collected on a filter, washed with water and dried.

Yd. : 60–65%

M.p. : 227°–228° C.

EXAMPLE 64:
4-METHYL-2,3-DIHYDRO-4H-PYRIDO[3,2-e][1,2,4]THIADIAZINE 1,1-DIOXIDE 0.08 g of NaBH$_4$ is added to a solution of 0.1 g of 4-methyl-4H-pyrido[3,2-e][1,2,4 ]thiadiazine 1,1- dioxide (Example 63) in 6 cm³ of isopropanol. The mixture is kept stirring at ambient temperature for 45 minutes. The solvent is then removed under partial vacuum and the residue is treated with 5 cm³ of water. The suspension obtained is adjusted to a pH of 7 and then extracted with chloroform (3 times 100 cm³). The organic phase is washed with water (25 cm³), dried (MgSO$_4$) and then concentrated to dryness to provide the title compound.

Yd. : 95–100%

M.p. : 208°–210° C.

EXAMPLE 65:
4-ETHYL-4H-PYRIDO[3,2-e][1,2,4]THIADIAZINE 1,1-DIOXIDE

The compound is obtained according to the same procedure as that described for Example 63, starting from 0. 1 g of 4H-pyrido[3,2-e][1,2,4]thiadiazine 1,1-dioxide (Example 16) and 0.17 g of ethyl bromide.

Yd. : 65–70%

M.p. : 154°–156° C.

EXAMPLE 66:
4-ETHYL-2,3-DIHYDRO-4H-PYRIDO[3,2-e][1,2,4]THIADIAZINE 1,1-DIOXIDE

The compound is obtained according to the same procedure as that described for Example 64, starting from 4-ethyl-4H-pyrido[3,2-e][1,2,4]thiadiazine 1,1,-dioxide (Example 65).

Yd. : 85–90%

M.p. : 190°–191° C.

EXAMPLE 67:
3,4-DIMETHYL-2,3-DIHYDRO-4H-PYRIDO[4,3-e][1,2,4]THIADIAZINE 1,1-DIOXIDE

A solution of 0.5 g of 4-methylaminopyridine-3- sulfonamide (Preparation 12) and 0.75 cm³ of acetaldehyde in 5 cm³ of isopropanol, to which 3 drops of a saturated solution of hydrochloric acid in ethyl acetate have been added, is heated for 2 hours at 50° C. The solvent is then removed under partial vacuum and the residue obtained is recrystallized first from isopropanol and then from methanol.

Yd. : 45–50%

M.p. : 189°–190° C.

EXAMPLE 68:
3-ETHYL-4-METHYL-2,3-DIHYDRO-4H-PYRIDO-[4,3-e][1,2,4]THIADIAZINE 1,1-DIOXIDE

A solution of 0.5 g of 4-methylaminopyridine-3- sulfonamide (Preparation 12) and 0.9 cm³ of propionaldehyde in 5 cm³ of isopropanol, to which 3 drops of a saturated solution of hydrochloric acid in ethyl acetate have been added, is heated for 3 hours at 50° C. The solvent is then removed under partial vacuum and the residue obtained is recrystallized several times from a chloroform/petroleum ether (⅓) mixture.

Yd. : 35–40%

M.p. : 147°–149° C.

EXAMPLE 69:
2-METHYL-2,3-DIHYDRO-4H-PYRIDO[3,2-e]-[1,2,4]THIADIAZINE 1,1-DIOXIDE 0.52 g of potassium carbonate and 0.94 g of iodomethane are added to a solution of 0.25 g of 2,3- dihydro-4H-pyrido [3,2-e][1,2,4]thiadiazine 1,1-dioxide (Example 1) in 10 cm³ of acetonitrile. The suspension is heated at 50° C. for 3 hours. The acetonitrile is then removed by evaporation under partial vacuum and the residue obtained is taken up in 10 cm³ of water. The suspension is extracted with chloroform (5 times 100 cm³). The extraction solvent is dried over MgSO$_4$ and then concentrated to dryness. The solid obtained is purified by chromatography on a silica column (elution solvent: 1/9 MeOH/CHCl$_3$).

Yd. : 60–65%

M.p. : 182°–183° C.

EXAMPLE 70:
2,4-DIMETHYL-2,3-DIHYDRO-4H-PYRIDO[4,3-e][1,2,4]THIADIAZINE 1,1-DIOXIDE

A solution of 0.25 g of 4-methyl-2,3-dihydro-4H- pyrido [4,3e][1,2,4]thiadiazine 1,1-dioxide (Example 5) in 8 cm³ of acetonitrile is treated with 0.5 g of potassium carbonate (±3 eq.) and then with 0.26 g of methyl p-toluenesulfonate (1.1 eq.). The suspension obtained is brought to reflux for 2 hours. The solvent is then removed by evaporation under reduced pressure and the residue is distributed between 10 cm³ of water and 100 ml of chloroform. The aqueous phase is then extracted twice with 50 cm³ of chloroform. The combined organic fractions are dried over MgSO₄, filtered and then concentrated to dryness. The residue is dissolved in the minimum amount of chloroform. The addition of an excess of petroleum ether (40°–60° C.) causes precipitation of the crystals of the title product. They are collected on the filter, washed with petroleum ether (40°–60° C.) and dried.

Yd. : 60–65%

M.p. : 167°–169° C.

EXAMPLE 71:
4-METHYL-2-PROPYL-2,3-DIHYDRO-4H-PYRIDO[4,3-e][1,2,4]THIADIAZINE 1,1-DIOXIDE

The title compound is obtained according to the procedure described in Example 70, starting from 4- methyl-2,3-dihydro-4H-pyrido[4,3e][1,2,4]thiadiazine 1,1-dioxide (Example 5), but using sodium hydride (2 eq.) and propyl bromide (3 eq.) in place of potassium carbonate and methyl p-toluenesulfonate respectively.

Yd. : 50–55%

M.p. : 130°–131° C.

EXAMPLE 72:
4-ISOPROPYL-2-METHYL-2,3-DIHYDRO-4H-PYRIDO[4,3-e][1,2,4]THIADIAZINE 1,1-DIOXIDE

The title compound is obtained according to the procedure described for Example 71, starting from 4- isopropyl-2,3-dihydro-4H-pyrido[4,3e][1,2,4]thiadiazine 1,1-dioxide (Example 3), but using methyl p-toluenesulfonate (1.5 eq.) in place of propyl bromide and limiting the duration of the reflux to 1 hour.

Yd. : 45–50%

M.p. : 159°–161° C.

EXAMPLE 73:
2,4-DIMETHYL-2,3-DIHYDRO-4H-PYRIDO[3,2-e]-[1,2,4]THIADIAZINE 1,1-DIOXIDE

The title compound is obtained according to the same procedure as that described for Example 69, starting from 0.3 g of 4-methyl-2,3-dihydro-4H-pyrido[3,2-e] [1,2,4]thiadiazine 1,1-dioxide (Example 64), 0.62 g of potassium carbonate and 0.63 g of iodomethane, the duration of the heating at 50° C. being limited to 1 hour and a half. The product obtained is converted to the hydrochloride after dissolving in 10 cm³ of ethyl acetate and adding 4 cm³ of ethyl acetate saturated with gaseous hydrochloric acid. The precipitate obtained is collected on a filter, washed with ethyl acetate and dried.

Yd. : 50–55%

M.p. (hydrochloride): 172°–173° C.

EXAMPLE 74:
4-ETHYL-2-METHYL-2,3-DIHYDRO-4H-PYRIDO[3,2-e][1,2,4]THIADIAZINE 1,1-DIOXIDE

The title compound is obtained according to the same procedure as that described for Example 70, starting from 4-ethyl-2,3-dihydro-4H-pyrido[ 3,2-e][1,2,4]thiadiazine 1,1-dioxide (Example 66).

Yd. : 60–65%

M.p. : 103°–104° C.

EXAMPLE 75:
6-METHYL-4H-PYRIDO[3,2-e][1,2,4]THIADIAZINE 1,1-DIOXIDE

A suspension of 1.3 g of 3-amino-5-methylpyridine-2-sulfonamide (Preparation 25) in 13 cm³ of ethyl orthoformate is brought to reflux for 2 hours. After cooling, the precipitate obtained is collected on a filter, washed with diethyl ether and dried.

Yd. : 95–100%

M.p. : 322°–324° C.

EXAMPLE 76:
4,6-DIMETHYL-4H-PYRIDO[3,2-e][1,2,4]-THIADIAZINE 1,1-DIOXIDE

A solution of 0.6 g of 6-methyl-4H-pyrido[3,2-e][1,2,4] thiadiazine 1,1-dioxide (Example 75) in 15 cm³ of acetonitrile is treated with 2.5 g of potassium carbonate and 0.9 g of methyl p-toluenesulfonate. After refluxing for 16 hours, the solvent is removed under partial vacuum and the solid obtained is taken up in 15 cm³ of water. The precipitate is collected on a filter, washed with water and dried.

Yd. : 75–80%

M.p. : 247°–249° C.

EXAMPLE 77:
4,6-DIMETHYL-2,3-DIHYDRO-4H-PYRIDO[3,2-e]-[1,2,4]THIADIAZINE 1,1-DIOXIDE

A solution of 0.5 g of 4,6-dimethyl-4H- pyrido[3,2-e][1,2,4]thiadiazine 1,1-dioxide (Example 76) in 25 cm³ of a 1/1 isopropanol/chloroform mixture is treated, in small portions, with 0.4 g of sodium borohydride with good stirring and under an inert atmosphere. After 30 minutes at ambient temperature, the excess borohydride is destroyed by addition of a few drops of acetic acid and the solvent is removed under reduced pressure. The residue is taken up in 10 cm³ of water and the pH of the mixture is brought to neutrality. The precipitate obtained is collected on a filter, washed with water and dried.

Yd. : 75–80%

M.p. : 220°–221° C.

EXAMPLE 78:
4-ETHYL-6-METHYL-4H-PYRIDO[3,2-e][1,2,4]-THIADIAZINE 1,1-DIOXIDE

A solution of 1.2 g of 6-methyl-4H-pyrido[3,2-e] [1,2,4] thiadiazine 1,1-dioxide (Example 75) in 15 cm³ of acetonitrile is treated with 2.5 g of potassium carbonate and 2 g of ethyl bromide. After refluxing for 16 hours, the solvent is removed under partial vacuum and the solid obtained is taken up in 15 cm³ of water. The precipitate is collected on a filter, washed with water and dried.

Yd. : 60–65%

M.p. : 185°–187° C.

EXAMPLE 79:
4-ETHYL-6-METHYL-2,3-DIHYDRO-4H-PYRIDO[3,2-e ][1,2,4]THIADIAZINE 1,1-DIOXIDE

A solution of 0.6 g of 4-ethyl-6-methyl-4H- pyrido[3,2-e][1,2,4]thiadiazine 1,1-dioxide (Example 78} in 30 cm³ of a 1/1 isopropanol/chloroform mixture is treated, in small portions, with 0.45 g of sodium borohydride with good stirring and under an inert atmosphere. After 30 minutes at ambient temperature, the excess borohydride is destroyed by addition of a few drops of acetic acid and the solvent is removed under reduced pressure. The residue is taken up in 10 cm³ of water and the pH of the mixture is brought to neutrality. The precipitate obtained is collected on a filter, washed with water and dried.

Yd. : 60–65%

M.p. : 146°–148° C.

EXAMPLE 80:
2,6-DIMETHYL-4-ETHYL-2,3-DIHYDRO-4H-PYRIDO[3,2-e][1,2,4]THIADIAZINE 1, 1-DIOXIDE

A solution of 0.2 g of 4-ethyl-6-methyl-2,3- dihydro-4H-pyrido[3,2-e] [1,2,4]thiadiazine 1,1-dioxide (Example 79) in 10 cm³ of acetonitrile is treated with 2 equivalents of NaOH and then brought to reflux for 15 minutes with stirring. The mixture is treated with 0.18 g of methyl p-toluenesulfonate and stirred for 2 hours at ambient temperature. The solvent is then removed under reduced pressure and the residue is taken up in 5 cm³ of water. The precipitate is collected on a filter, washed with water and dried. It is purified by chromatography on a silica column (1/1 chloroform/diethyl ether).

Yd. : 50–55%

M.p. : 121°–122° C.

EXAMPLES 81 to 83:
4-ETHYL-2-ALKYL(ARYL)OXYCARBONYL-2,3-DIHYDRO-4H-PYRIDO[3,2-e][1,2,4]THIADIAZINE 1,1-DIOXIDE

General procedure:

$9.4 \times 10^{-4}$ mol of 4-ethyl-2,3-dihydro-4H- pyrido[3,2-e][1,2,4]thiadiazine 1,1-dioxide (Example 66), $3.8 \times 10^{-3}$ mol (4 equivalents) of potassium carbonate and 17 cm³ of acetonitrile are introduced into a 50 cm³ round- bottomed flask. $1.3 \times 10^{-3}$ mol (1.2 equivalents) of alkyl (or aryl) chloroformate are added to this suspension with stirring. After 4 hours at ambient temperature, the insoluble material (potassium carbonate) is removed by filtration and the filtrate is concentrated to dryness under reduced pressure. The residue is taken up in 10 cm³ of petroleum ether (40°–60° C.), dried, washed with water and dried again. The compounds thus obtained are pure.

EXAMPLE 81:
4-ETHYL-2-METHYLOXYCARBONYL-2,3-DIHYDRO-4H-PYRIDO[3,2-e][1,2,4]THIADIAZINE 1, 1-DIOXIDE

Yd. : 70–75%

M.p. : 138°–140° C.

EXAMPLE 82:
4-ETHYL-2-ETHYLOXYCARBONYL-2,3-DIHYDRO-4H-PYRIDO[3,2-e][1,2,4]THIADIAZINE 1,1-DIOXIDE

Yd. : 60–65%

M.p. : 50°–55° C. (decomposition)

EXAMPLE 83:
4-ETHYL-2-PHENYLOXYCARBONYL-2,3-DIHYDRO-4H-PYRIDO[3,2-e]e][1,2,4]THIADIAZINE 1,1-DIOXIDE

Yd. : 50–55%

M.p. : 90°–95° C. (decomposition)

PHARMACOLOGICAL EXAMPLES

EXAMPLE A: Study of the excitatory currents induced by AMPA in Kenopus ovocytes a) Method:

mRNAs are prepared from male Wistar rat cerebral cortex by the guanidinium thiocyanate/phenol/chloroform method. Poly A+ mRNAs are isolated by chromatography on oligo-dT cellulose and injected in a proportion of 50 ng per ovocyte. The ovocytes are left to incubate for 2 to 3 days at 18° C. to enable expression of the receptors and are then stored at 8°–10° C.

Electrophysiological recording is carried out in a Plexiglass® chamber at 20°–24° C. in OR2 medium (J. Exp. Zool., 1973, 184, 321–334) by the voltage-clamp method with 2 electrodes, a third electrode placed in the bath being used as reference. All the compounds are applied via the incubation medium and the electrical current is measured at the end of the application period. AMPA is used at a concentration of 30 µM. The concentration doubling (EC2X) or quintupling (EC5X) the intensity of the current induced by AMPA alone (50 to 100 nA) is characterized for each compound studied.

b) Results: The compounds of the invention very strongly potentiate the excitatory effects of AMPA and their activity is very markedly greater than the reference compounds, as shown in the table below:

|  | EC2X (µM) | EC5X (µM) |
|---|---|---|
| Diazoxide | 400 | 1000 |
| Aniracetam | 1300 | 5000 |
| Exemple 12 | 200 | 400 |
| Exemple 25 | 250 | 800 |
| Exemple 5 | 50 | 300 |
| Exemple 3 | 90 | 250 |
| Exemple 8 | 200 | 500 |
| Exemple 14 | 300 | 400 |
| Exemple 49 | 500 | 800 |
| Exemple 64 | 29 | 37 |
| Exemple 66 | 10 | 16 |

EXAMPLE B: Study of the synaptic excitatory potentials induced by electrical stimulation of hippocampus sections a) Method:

Transverse hippocampus sections (500 µM) from male Wistar rats are prepared using a tissue chopper and are then incubated for 45 minutes in a calcium-free medium containing 10 mM $Mg^{++}$. They are then stabilized in Krebs adjusted to a pH of 7.35 and oxygenated with $O_2/CO_2$ (95%/5%) at ambient temperature.

The sections are submersed at 35° C. and the post-synaptic excitatory potentials (PSEPs) are recorded in the dendritic field of granular cells of the gyrus dentatus during stimulation (50–100 µA, 50 µsec) every 30 seconds of the perforating route by a bipolar tungsten electrode.

The acquisition and the analysis of the PSEPs are carried out by virtue of an A-D converter, a TL-1 interface and "pCLAMP" software.

The amplitude and the duration of the PSEPs are evaluated on the negative wave with respect to the base current.

The compounds are applied for 10 to 20 minutes in the superfusion bath containing MgSO$_4$ (1 mM) in order to block activation of the NMDA receptors. The concentration which increases by 50% the amplitude (A50) or the duration (D50) of the PSEP is characterized for each compound.

b) Results:

The compounds of the invention increase the duration of the PSEP at lower doses than the reference compounds, as shown in the following table:

|  | D50(µM) |
|---|---|
| Aniracetam | 3000 |
| Diazoxide | 560 |
| Exemple 12 | 100 |
| Exemple 5 | 130 |
| Exemple 3 | 240 |
| Exemple 49 | 300 |

Moreover, the compounds of the invention exert novel effects with respect to the reference compounds and especially diazoxide. In fact, the latter exerts its excitatory effects more with respect to the duration of the PSEP, as shown by the D50/A50 ratio, which is equal to 0.5. In contrast, the derivatives of the invention can either preferentially increase the duration or preferentially the amplitude, as is shown in the following table:

|  | D50/A50 |
|---|---|
| Diazoxide | 0,5 |
| Exemple 5 | 0,6 |
| Exemple 12 | 0,65 |
| Exemple 3 | 0,9 |
| Exemple 14 | 1,25 |
| Exemple 49 | 1,55 |

EXAMPLE C: Study of the effects which facilitate cerebral excitation induced by an auditory stress in DBA2 mice a) Method:

DBA2 mice (Iffa-Credo, l'Arbresic, France), aged from 21 to 26 days, are subjected to a sound stress in an insulated enclosure.

This stress brings about symptoms of excitation and then convulsions if it is applied at high intensity (1,400 Hz, 100 dB). These behavioral results are antagonized by compounds which block glutamatergic neurotransmission.

When applied at low frequency (1,800 Hz, 100 dB), the sound stress brings about few or no excitation symptoms.

Compounds which facilitate glutamatergic neurotransmission can potentiate these symptoms which are then categorized from 1 to 4 for each animal according to their intensity.

Each group of animals (n=10) receives the compound by the IP route 30 minutes before the sound stress. A control group (n=10) receives the solvent.

The dose which doubles the excitation result with respect to the control result is measured.

b) Result:

In vitro potentiation of the currents induced by AMPA is expressed in vivo since the compound of Example 66, whose EC2X value is 10 µM, doubles the excitation result at a dose of 1 mg/kg IP. Under the same administration conditions, diazoxide and aniracetam are inactive.

EXAMPLE D: Search for toxic effects

The compounds of the invention, when administered by the oral route, do not bring about either mortality or behavioral symptoms indicating toxicity, up to the maximum dose tested of 300 mg/kg.

We claim:

1. A compound which is selected from those of formula (I):

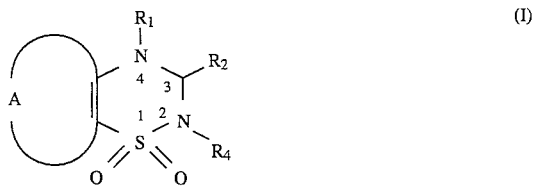

in which:

R$_1$ represents a group chosen from:
hydrogen,
R$_3$, with R$_3$ representing a radical chosen from lower alkyl, lower alkenyl and lower alkynyl, R$_3$ being unsubstituted or substituted,
cycloalkyl,
substituted cycloalkyl,
lower cycloalkylalkyl,
substituted lower cycloalkylalkyl,
lower acyl,
lower alkoxycarbonyl,
arylcarbonyl which is unsubstituted or substituted on the aryl ring,
and aryloxycarbonyl which is unsubstituted or substituted on the aryl ring,
or R$_1$ forms, between the 3 or 4 atoms of the thiadiazine ring present in the formula (I), a double bond;

R$_2$ represents a group chosen from:
hydrogen,
R$_{10}$, with R$_{10}$ having the same definition as R$_3$ above, R$_{10}$ being unsubstituted or substituted,
R$_{11}$, with R$_{11}$ representing a group chosen from cycloalkyl, lower cycloalkylalkyl, bicycloalkyl and lower bicycloalkylalkyl, R$_{11}$ being unsubstituted or substituted,
—O—R$_{10}$, with R$_{10}$ as defined above,
thioxo,
—S—R$_{12}$, in which R$_{12}$ represents a lower alkyl, R$_{12}$ being unsubstituted or substituted,
aryl,
substituted aryl, and

in which R$_8$ and R$_9$ represent, independently of one another, a radical chosen from:
hydrogen,
lower alkyl,
cycloalkyl,
lower cycloalkylalkyl,
and a heterocycle R$_{13}$ chosen from pyrrolidine, piperidine, piperazine, morpholine and thiomorpholine;
or $R_8$ and $R_9$ form, together with the nitrogen atom which carries them, a heterocycle $R_{13}$ as defined above, $R_4$ represents a group chosen From:
hydrogen,
$R_{14}$, $R_{14}$ having the same definition as $R_3$ above, $R_{14}$ being unsubstituted or substituted,
cycloalkyl,
aryl,
substituted aryl,
lower acyl,
lower alkoxycarbonyl,
arylcarbonyl, unsubstituted or substituted on the aryl ring,
and aryloxycarbonyl, unsubstituted or substituted on the aryl ring, or $R_4$ forms, between the 2 and 3 atoms of the thiadiazine ring present in the formula (I), a double bond;

A forms, with the two carbon atoms which carry it, a pyridine ring chosen from the $A_1$, $A_2$, $A_3$ and $A_4$ groups:

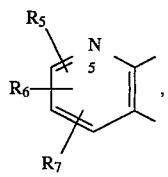  (A₁)

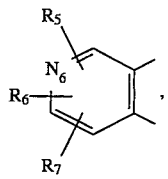  (A₂)

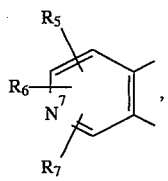  (A₃)

and

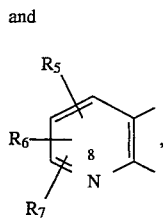  (A₄)

in which $R_5$, $R_6$ and $R_7$ represent, independently of one another, a radical chosen from: hydrogen, halogen, lower alkyl, hydroxyl, mercapto, lower alkoxy, lower alkylthio, trifluoromethyl, carboxyl, lower acyl, aryl, lower arylalkyl, amino, lower alkylamino, and lower dialkylamino, it being understood that, when A represents an unsubstituted group of formula $A_1$, $R_2$ represents hydrogen, amino or methyl, and $R_5$, $R_6$ and $R_7$ simultaneously represent hydrogen, then $R_1$ cannot be hydrogen or methyl, it being understood that, except when otherwise specified, "lower alkyl", "lower alkoxy", "lower acyl" and "lower alkylthio" mean linear or branched groups having 1 to 6 carbon atoms, inclusive, "lower alkenyl" means a linear or branched group containing 2 to 6 carbon atoms having 1 or 2 double bonds, inclusive, "lower alkynyl" means a linear or branched group containing 2 to 6 carbon atoms having 1 or 2 triple bonds, inclusive, "cycloalkyl" means a cyclic group having 3 to 8 carbon atoms, inclusive, "bicycloalkyl" means a bicyclic group having 6 to 12 carbon atoms, inclusive, "aryl" means phenyl or naphthyl, "substituted" in association with $R_3$, $R_{10}$ and $R_{14}$ groups, means that these groups are substituted by one or a number of radicals chosen from halogen, hydroxyl, and lower alkoxy, "substituted", in association with "cycloalkyl", "cycloalkylalkyl" and $R_{11}$ groups, means that this group thus is substituted by one or a number of radicals chosen from hydroxyl, lower alkyl, and lower alkoxy or is substituted by an oxo group, "substituted", in association with aryl means that this group is substituted by one or a number of radicals chosen from halogen, hydroxyl, lower alkyl, lower alkoxy, and trifluoromethyl, its optical isomers, and its addition salts with a pharmaceutically acceptable acid or base.

2. A compound as claimed in claim 1 which is 4-isopropyl-2,3-dihydro-4H-pyrido [4,3-e][1,2,4]thiadiazine 1,1-dioxide.

3. A compound as claimed in claim 1 which is 3,4-dimethyl-4H-pyrido [4,3-e][1,2,4]thiadiazine 1,1-dioxide.

4. A compound as claimed in claim 1 which is 4-methyl-2,3-dihydro-4H-pyrido[ 4,3-e][1,2,4]thiadiazine 1,1-dioxide.

5. A compound as claimed in claim 1 which is 2,3-dimethyl-2,3-dihydro-4H-pyrido [4,3-e][1,2,4]thiadiazine 1,1-dioxide.

6. A compound as claimed in claim 1 which is 4-methyl-2,3-dihydro-4H-pyrido[ 3,2-e][1,2,4]thiadiazine 1,1-dioxide.

7. A compound as claimed in claim 1 which is 4-ethyl-2,3-dihydro-4H-pyrido[ 3,2-e][1,2,4]thiadiazine 1,1- dioxide.

8. A compound as claimed in claim 1 which is 6-chloro-2,3-dihydro-4H-pyrido [4,3-e][1,2,4]thiadiazine 1,1-dioxide.

9. A compound as claimed in claim 1 which is 2-methyl-2,3-dihydro-4H-pyrido [3,2-e ][1,2,4 ]thiadiazine 1,1-dioxide.

10. A pharmaceutical composition useful in treating glutamatergic neurotransmission dysfunction containing a compound of claim 1, in combination with a pharmaceutically-acceptable excipient or vehicle.

11. A method of treating a mammal afflicted with a memory and cognitive disorder, comprising the step of administering to the said mammal an amount of a compound as claimed in claim 1 which is effective for alleviation of said disorder.

12. A method of treating a mammal afflicted with a memory and cognitive disorder comprising the step of administering to the said mammal an amount of a compound which is effective for alleviation of the disorder and selected from those of formula (I):

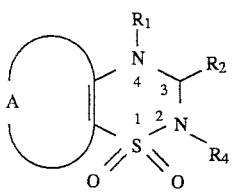 (I)

in which:

R₁ represents a group chosen from;
hydrogen,
R₃, with R₃ representing a radical chosen from lower alkyl, lower alkenyl and lower alkynyl, R₃ being unsubstituted or substituted,
cycloalkyl,
substituted cycloalkyl,
lower cycloalkylalkyl,
substituted lower cycloalkylalkyl,
lower acyl,
lower alkoxycarbonyl,
arylcarbonyl which is unsubstituted or substituted on the aryl ring,
and aryloxycarbonyl which is unsubstituted or substituted on the aryl ring,
or R₁ forms, between the 3 or 4 atoms of the thiadiazine ring present in the formula (I), a double bond;

R₂ represents a group chosen from:
hydrogen,
R₁₀, with R₁₀ having the same definition as R₃ above, R₁₀ being unsubstituted or substituted,
R₁₁, with R₁₁ representing a group chosen from cycloalkyl, lower cycloalkylalkyl, bicycloalkyl and lower bicycloalkylalkyl, R₁₁ being unsubstituted or substituted,
—O—R₁₀, with R₁₀ as defined above,
thioxo,
—S—R₁₂, in which R₁₂ represents a lower alkyl, R₁₂ being unsubstituted or substituted,
aryl,
substituted aryl,
and

in which R₈ and R₉ represent, independently of one another, a radical chosen from:
hydrogen,
lower alkyl,
cycloalkyl,
lower cycloalkylalkyl,
and a heterocycle R₁₃ chosen from pyrrolidine, piperidine, piperazine, morpholine and thiomorpholine;
or R₈ and R₉ form, together with the nitrogen atom which carries them, a heterocycle R₁₃ as defined above, R₄ represents a group chosen from:
hydrogen,
R₁₄, R₁₄ having the same definition as R₃ above, R₁₄ being unsubstituted or substituted,
cycloalkyl,
aryl,
substituted aryl,
lower acyl,
lower alkoxycarbonyl,
arylcarbonyl, unsubstituted or substituted on the aryl ring,
and aryloxycarbonyl, unsubstituted or substituted on the aryl ring, or
R₄ forms, between the 2 and 3 atoms of the thiadiazine ring present in the formula (I), a double bond;

A forms, with the two carbon atoms which carry it, a pyridine ring chosen from the A₁, A₂, R₃ and A₄ groups:

 (A₁)

 (A₂)

 (A₃)

and

 (A₄)

in which R₅, R₆ and R₇ represent, independently of one another, a radical chosen from: hydrogen, halogen, lower alkyl, hydroxyl, mercapto, lower alkoxy, lower alkylthio, trifluoromethyl, carboxyl, lower acyl, aryl, lower arylalkyl, amino, lower alkylamino, and lower dialkylamino, it being understood that, except when otherwise specified,
"lower alkyl", "lower alkoxy", "lower acyl" and "lower alkylthio" mean linear or branched groups having 1 to 6 carbon atoms, inclusive,
"lower alkenyl" means a linear or branched group containing 2 to 6 carbon atoms having 1 or 2 double bonds, inclusive,
"lower alkynyl" means a linear or branched group containing 2 to 6 carbon atoms having 1 or 2 triple bonds, inclusive,
"cycloalkyl" means a cyclic group having 3 to 8 carbon atoms, inclusive,
"bicycloalkyl" means a bicyclic group having 6 to 12 carbon atoms, inclusive,
"aryl" means phenyl or naphthyl,
"substituted", in association with R₃, R₁₀ and R₁₄ groups, means that these groups are substituted by one or a number of radicals chosen from halogen, hydroxyl, and lower alkoxy,
"substituted", in association with "cycloalkyl", "cycloalkylalkyl" and $R_{11}$ groups, means that this group is substituted by one or a number of radicals chosen from hydroxyl, lower alkyl, and lower alkoxy or is substituted by an oxo group, "substituted", in association with aryl, means that this group is substituted by one or a number of radicals chosen from halogen, hydroxyl, lower alkyl, lower alkoxy, and trifluoromethyl, its optical isomers, and its addition salts with a pharmaceutically-acceptable acid or base.

13. The method as claimed in claim 12 wherein the compound is 4-methyl-2,3-dihydro-4H-pyrido[2,3-e][1,2,4]thiadiazine 1,1-dioxide.

14. The method as claimed in claim 12 wherein the compound is 3-methyl-2,3-dihydro-4H-pyrido[3,2-e][1,2,4]thiadiazine 1,1-dioxide.

* * * * *

UNITED STATES PATENT AND TRADEMARK OFFICE
CERTIFICATE OF CORRECTION

PATENT NO. : 5,459,138
DATED : Oct. 17, 1995
INVENTOR(S) : Bernard Pirotte, Pascal de Tullio, Bernard Masereel, Jacques Delarge, Jean Lepagnol, Pierre Renard It is certified that error appears in the above-indentified patent and that said Letters Patent is hereby corrected as shown below:

Title Page, [56] Other Publications, Column 2, 10 lines from top: "[2,3-3]" should read -- [2,3-e] --.

Column 2, line 26: "substituted aryl," should read -- substituted aryl, and --.

Column 17, line 46: Delete second "5". Pg. 30, line 5

Column 19, line 21: "[1,2,4]THIADIAZINE" should read -- [1,2,4]THIADIAZINE 1,1-DIOXIDE --

Column 19, line 23: Delete "1,1-DIOXIDE".

Column 19, line 26: "Yd.:65-70%" and M.p (hydrochloride): 254-255° C." should be on separate lines (similar to all others.)

Column 21, line 33: "[1,2,4thiadiazine" should read -- [1,2,4]thiadiazine --.

Column 26, line 12: "[3,2e]" should read -- [3,2-e] --.

Column 26, line 43: "[4,3e]" should read -- [4,3-e] --.

UNITED STATES PATENT AND TRADEMARK OFFICE
CERTIFICATE OF CORRECTION

PATENT NO. : 5,459,138
DATED : Oct. 17, 1995                    Page 2 of 3
INVENTOR(S) : Bernard Pirotte, Pascal de Tullio, Bernard Masereel, Jacques Delarge, Jean Lepagnol, Pierre Renard It is certified that error appears in the above-indentified patent and that said Letters Patent is hereby corrected as shown below:

Column 27, line 9: "[4,3 -e]" should read -- [4,3-e] --.

Column 28, line 12: "[4,3e]" should read -- [4,3-e] --.

Column 30, line 37: "-3sulfonamide" should read -- -3-sulfonamide --.

Column 32, line 63: "[4,3e]" should read -- [4,3-e].

Column 33, line 19: [4,3e] should read -- [4,3-e].

Column 33, line 28: "1," at end of line should read -- 1,1-DIOXIDE --.

Column 33, line 29: Delete "1-DIOXIDE".

Column 33, line 33: "[4,3e]" should read -- [4,3-e] --.

Column 33, line 64: "[ 3,2-e]" should read -- [3,2-e] --.

Column 35, line 11: Add -- 1- -- to end of line.

Column 35, line 12: Delete "1-" at beginning of the line.

UNITED STATES PATENT AND TRADEMARK OFFICE
CERTIFICATE OF CORRECTION

PATENT NO. : 5,459,138
DATED : Oct. 17, 1995
INVENTOR(S) : Bernard Pirotte, Pascal de Tullio, Bernard Masereel, Jacques Delarge, Jean Lepagnol, Pierre Renard It is certified that error appears in the above-indentified patent and that said Letters Patent is hereby corrected as shown below:

Column 36, line 4: "Kenopus" should read -- Xenopus --.

Column 40, line 18: Delete "thus". (Claim 1, line 6).

Column 40, line 27: Add a "-" (dash) after pharmaceutically.

Signed and Sealed this

Thirtieth Day of January, 1996

Attest:

BRUCE LEHMAN

*Attesting Officer*      *Commissioner of Patents and Trademarks*